United States Patent [19]
Chan

[11] Patent Number: 6,143,006
[45] Date of Patent: Nov. 7, 2000

[54] APPARATUS AND METHOD FOR TYING AND TENSIONING KNOTS

[76] Inventor: Kwan-Ho Chan, 4803 1st Pl., Lubbock, Tex. 79410

[21] Appl. No.: 09/293,539

[22] Filed: Apr. 16, 1999

Related U.S. Application Data

[60] Provisional application No. 60/125,125, Mar. 19, 1999, provisional application No. 60/082,270, Apr. 18, 1998, and provisional application No. 60/111,402, Dec. 8, 1998.

[51] Int. Cl.[7] .................................................. A61B 17/04
[52] U.S. Cl. .......................... 606/148; 606/144; 289/1.2; 289/1.5; 289/17
[58] Field of Search ..................................... 606/139, 144, 606/148; 289/1.2, 1.5, 17

[56] References Cited

U.S. PATENT DOCUMENTS

| | | | |
|---|---|---|---|
| 5,397,326 | 3/1995 | Mangum | 606/148 |
| 5,405,352 | 4/1995 | Weston | 606/148 |
| 5,562,684 | 10/1996 | Kammerer | 606/139 |
| 5,591,177 | 1/1997 | Lehrer | 606/139 |

*Primary Examiner*—Gary Jackson
*Attorney, Agent, or Firm*—Pandiscio & Pandiscio

[57] ABSTRACT

A knot tier and method for advancing, tightening and locking a sliding knot.

29 Claims, 28 Drawing Sheets

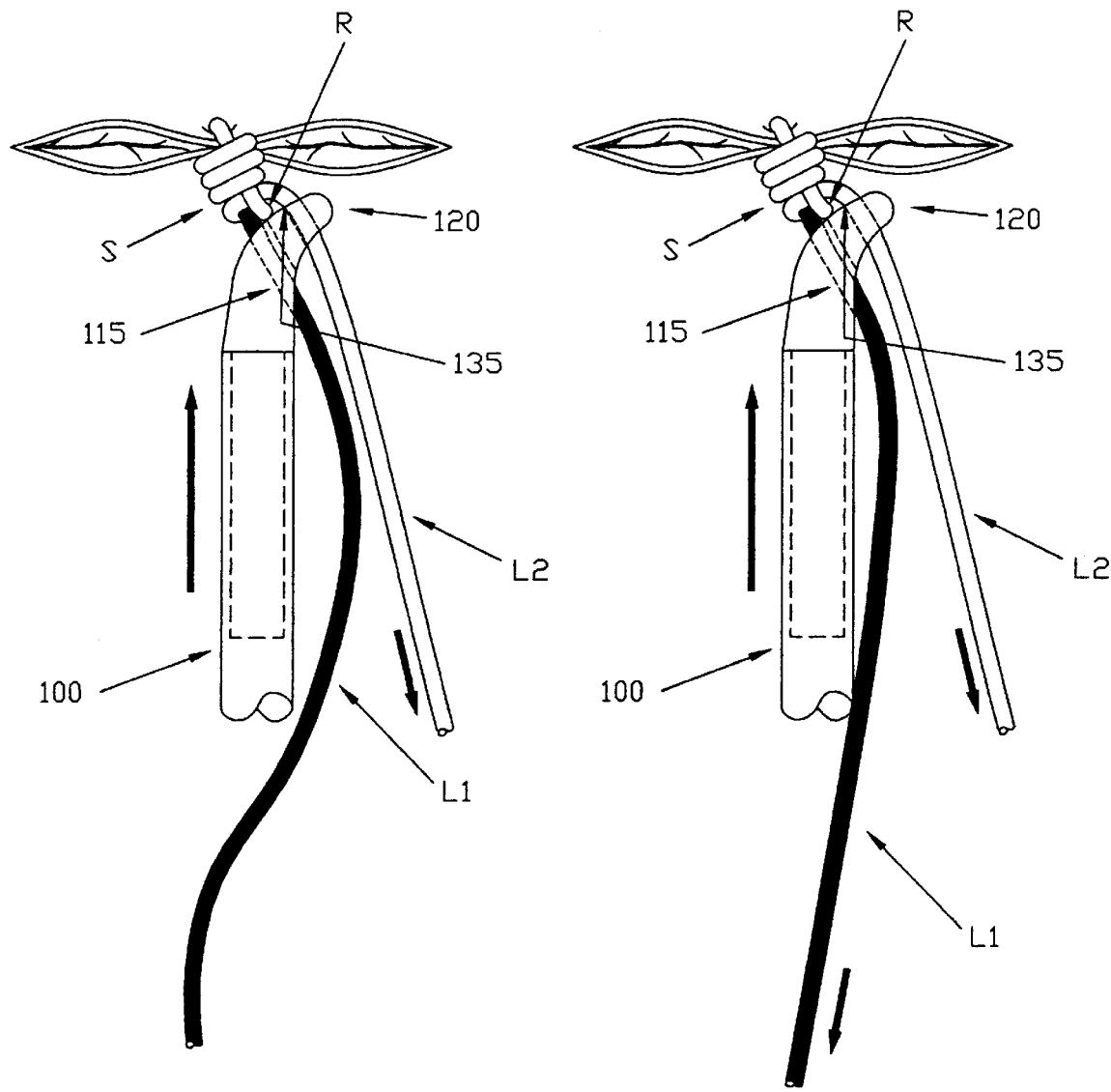

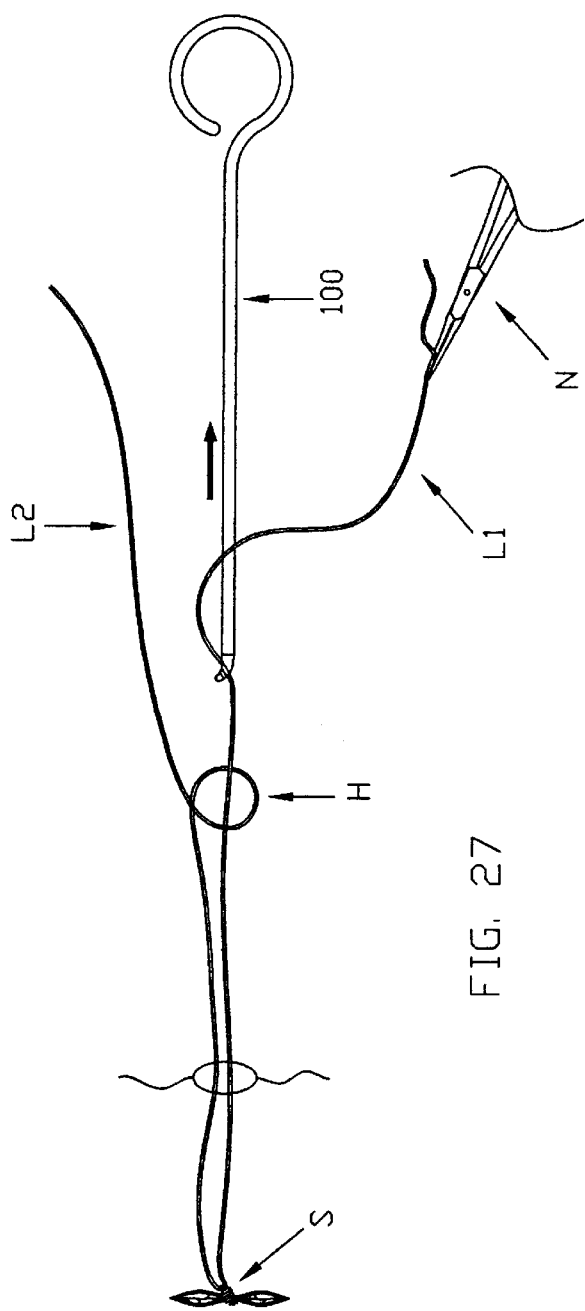
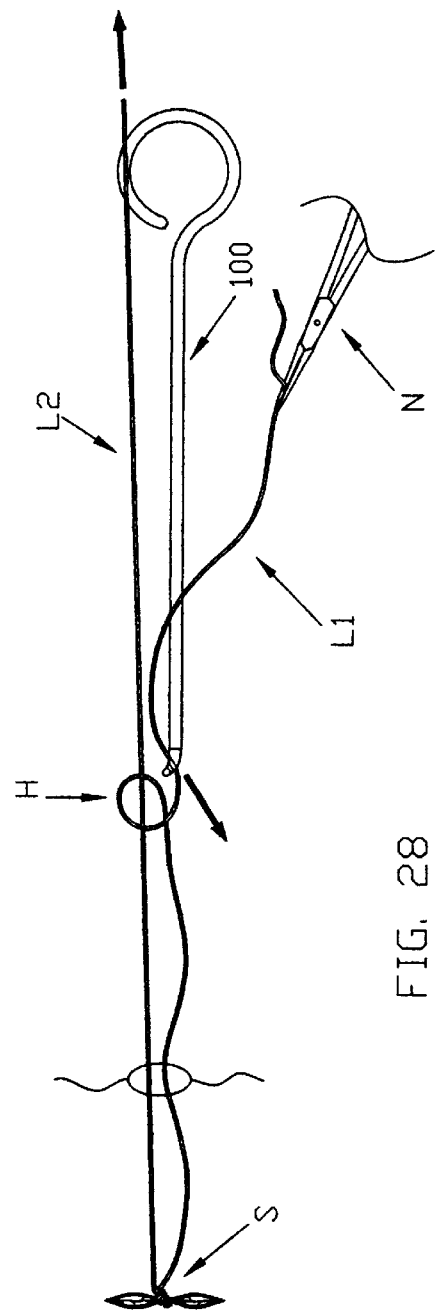
FIG. 27
FIG. 28

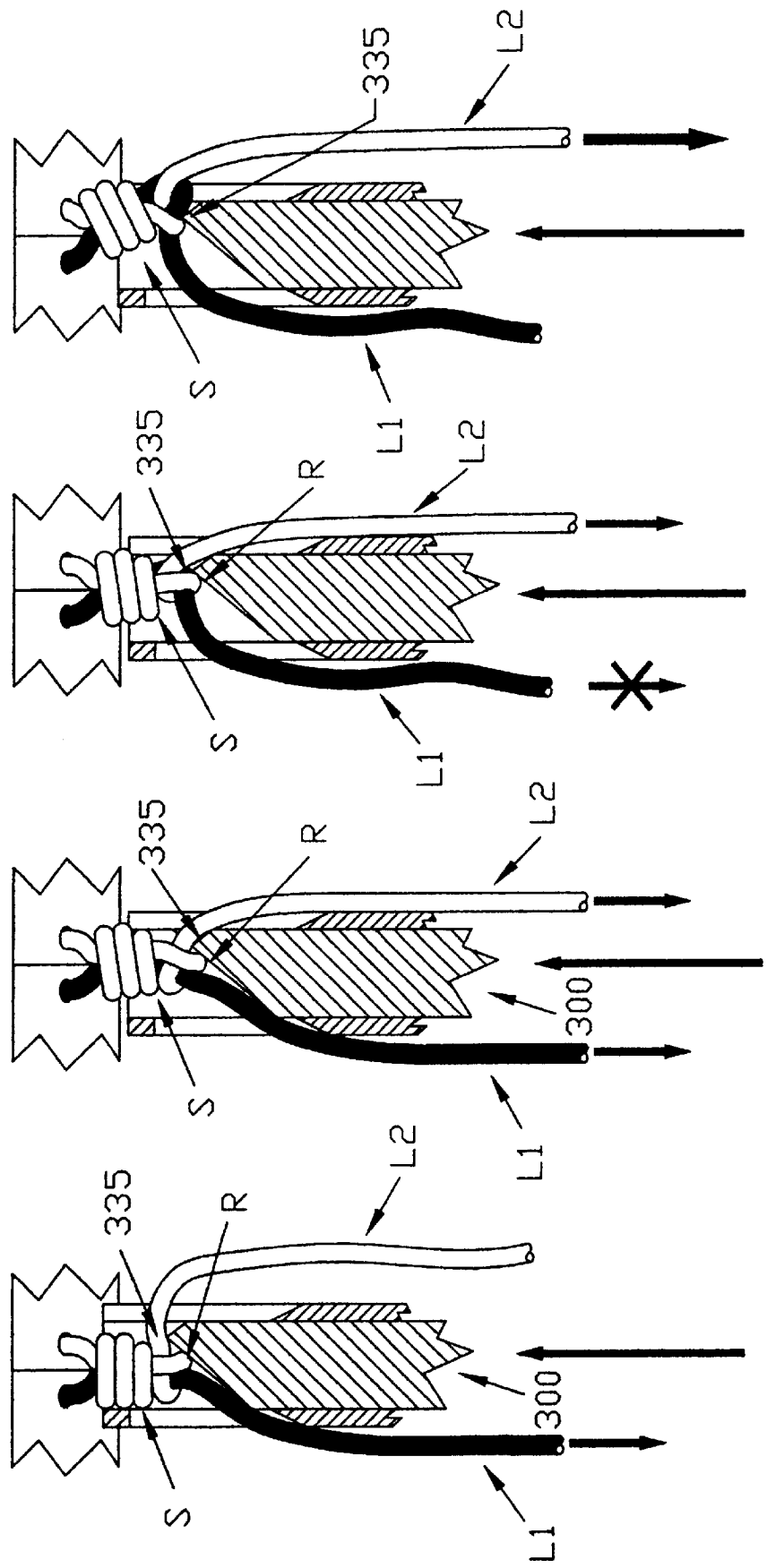

APPARATUS AND METHOD FOR TYING AND TENSIONING KNOTS

REFERENCE TO EARLIER PATENT APPLICATIONS

This patent application claims the benefit of:

(1) pending prior U.S. Provisional Patent Application Ser. No. 60/125,125, filed Mar. 19, 1999 by Kwan-Ho Chan for APPARATUS AND METHOD FOR TYING AND TENSIONING KNOTS; and (2) pending prior U.S. Provisional Patent Application Ser. No. 60/082,270, filed Apr. 18, 1998 by Kwan-Ho Chan for APPARATUS AND METHOD FOR TYING AND TENSIONING KNOTS; and (3) pending prior U.S. Provisional Patent Application Ser. No. 60/111,402, filed Dec. 8, 1998 by Kwan-Ho Chan for APPARATUS AND METHOD FOR TYING AND TENSIONING KNOTS.

The three aforementioned documents are hereby incorporated herein by reference.

FIELD OF THE INVENTION

The present invention relates to surgical instruments for securing sutures in tissue, and more particularly to tying secure knots under the desired tension at a location remote from the entry portals.

BACKGROUND OF THE INVENTION

1. Some Key Words and Definitions

Sliding Knot—A knot which allows sliding of the wrappings of the knot along a substantially straight portion of the suture limb to tighten the loop.

Post Limb—The straight portion of the suture limb upon which the second limb wraps around to form a sliding knot. A loosely equivalent term sometimes used in the art of knot tying is the "standing part".

Primary Post Limb—The post limb of the first sliding knot.

Wrapping Limb—The free portion of the suture limb that wraps around the post limb to form a sliding knot. Some loosely equivalent terms sometimes used in the art of knot tying are "working end", "running end" or "free end".

Half-hitch—The half-hitch knot is the simplest of all the sliding knot. It is formed by wrapping the suture limb once around the post limb of the suture (one turn). The half-hitch is commonly named either as "under-over" or "over-under" according to the position of the wrapping limb relative to the post limb during the knot forming process.

Direction of Half-hitches—Refers to whether the half-hitch is formed in the over-under sequence or the under-over sequence. Thus if the first half-hitch is an over-under half hitch and the second half-hitch is an under-over half-hitch, the second half-hitch is said to be in the reversed direction to that of the first half-hitch.

Reversing Half-hitches—Refers to two sequential half-hitches tied in reversed direction either on the same post or on the opposite post.

Compound Sliding Knot—A sliding knot that has more than one turn of the wrapping limb, i.e., any sliding knot other than a half-hitch is a compound sliding knot.

Forward Half Flip—The process whereby a half-hitch is converted to a knot with symmetrical throws by applying equal tension to both suture limbs in opposite directions (see transformation of knot going from FIG. 2 to FIG. 1).

Reverse Half Flip—The process whereby a knot with symmetrical throw is converted to a half hitch by releasing tension on one suture limb and applying tension to the other limb. The limb to which tension is applied becomes the post limb (see transformation of knot going from FIG. 1 to FIG. 2).

Full Flip—The process whereby a half-hitch is converted to another type of half-hitch in which the post limbs are switched. This is accomplished by applying tension on the wrapping limb and releasing the tension on the post limb. Note that an "under-over" half-hitch is converted to an "over-under" half-hitch during a full flip (see transformation of knot going from FIG. 3 to FIG. 4 and vice versa).

Primary Knot—This is the first knot that is tied extracorporeally and then transferred to the surgical site by a knot rundown device (sometimes also referred to as a knot tier or knot tensioner). The primary knot can either be a half-hitch, a compound sliding knot, or a double throw symmetrical knot.

2. Discussion

Tying square knots arthroscopically is difficult. As an alternative, sliding knots and half-hitches are frequently used in arthroscopic surgery.

FIGS. 1–13 illustrate various knot tying configurations common in arthroscopic surgery. More particularly, where a first piece of tissue T1 is to be secured to a second piece of suture T2 using a first suture limb L1 and a second suture limb L2, a sliding knot S (FIG. 5) may be formed on the two suture limbs and run down the post limb (L1 in FIG. 5) so as to cinch closed the loop P and thereby bind the tissues T1 and T2 together. In a sliding knot S, the wrapping limb (L2 in FIG. 5) typically forms a shoulder R at the proximal end of the sliding knot S.

In FIGS. 1–13, FIG. 1 illustrates a symmetrical throw; FIG. 2 illustrates an over-under half-hitch; FIG. 3 illustrates an under-over half-hitch; FIG. 4 is the same as FIG. 2; FIG. 5 illustrates various components of a generic lockable sliding knot; FIG. 6 illustrates an overhand throw non-locking sliding knot; FIG. 7 illustrates a modified Duncan loop non-locking sliding knot; FIG. 8 illustrates a distal locking Roeder knot; FIG. 9 illustrates a proximal locking tautline hitch knot; FIG. 10 illustrates an overhand throw sliding knot with locking half-hitches; FIG. 11 illustrates a modified Duncan loop sliding knot with locking half-hitches; FIG. 12 illustrates a Roeder sliding knot with locking half-hitches; and FIG. 13 illustrates a tautline hitch sliding knot with locking half-hitches.

For secure arthroscopic rotator cuff and Bankart repairs, not only must the knot be securely tied but the loop of the knot has to be tied under the desired tension in order to coapt the tissue edges. The current recommended arthroscopic knot tying technique using an initial sliding knot requires that the sliding knot be locked with reversing half-hitches on alternating posts (see, for example, FIGS. 10–13). However, the tension in the loop of the primary sliding knot may slip inadvertently during post-switching. Current knot tying techniques using prior art knot tiers and methods cannot predictably or reliably tie knots under tension.

More particularly, sliding knots tied extracorporeally can be advanced to a repair site inside the body cavity by simply pulling on the post limb. However, pulling on the post limb will cause undesirable traction on the tissue being repaired. As a result, most surgeons would prefer to advance the sliding knot by pushing the sliding knot forward with a knot tier device when pulling on the post limb. In this way the sliding knot can be advanced without undue tension on the tissue. When the knot abuts against the tissue, the margins of the tissue are drawn together by pulling on the post limb and by pushing against the sliding knot with the tip of a knot tier.

However, when tension in the post limb is released, the sliding knot has a tendency to back off due to the resiliency of the soft tissue, particularly in contracted soft tissue such as is often encountered in rotator cuff repairs.

More particularly, as noted above, in prior art techniques the sliding knot is locked by adding reversing half-hitches on alternating posts (see, for example, FIGS. 10–13). However, one deficiency of these prior art methods is that when tension is released on the primary post limb in order to add the first half-hitch on the opposite post, the primary sliding knot backs off before the first half-hitch is formed to lock the primary sliding knot. In other words, prior art knot tier devices and methods cannot lock sliding knots prior to post switching.

A survey of surgical literature indicates that a variety of different sliding knots are used in arthroscopic and laparoscopic surgery. A detailed examination of the construction of these knots shows that each knot can be classified as either non-lockable sliding knots (see FIGS. 6 and 7) or lockable sliding knots (FIGS. 8 and 9). The lockable knots can be further subdivided into distal locking knots (FIG. 8) and proximal locking knots (FIG. 9). In the distal locking knot, tension on the wrapping limb distorts the distal post portion of the knot (FIG. 8), whereas in the proximal locking knot, tension on the wrapping limb distorts the proximal post portion of the knot (FIG. 9). The resistance to knot slippage is increased by the bend in the distorted post portion of the knot. The preventative measures that can be taken to minimize the sliding knot from backing off relates to the classification of the sliding knot.

Backing off in all sliding knots, irregardless of the classification, can be minimized by simply "cinching" the wrappings around the post. Many of the non-locking sliding knots such as the modified Duncan loop (see, for example, FIG. 7) have several wrappings around the initial post and slippage is prevented by tightening the grip of these wrappings. In the lockable sliding knots, pulling on the wrapping limb distorts the post limb. The bend in the distorted post resists the knot from backing off. The disadvantage of the distal locking knot is the difficulty in locking the knot when tension in the knot loop is high. The advantage of the proximally locking knot is the ease with which the knot can be locked under the desired loop tension.

All non-locking knots can be converted to proximal locking knots by stacking a half-hitch knot proximally.

With the current recommended arthroscopic knot tying technique, even the so-called lockable sliding knots are further locked with reversing half-hitches prior to conclusion of the suturing process.

OBJECTS OF THE INVENTION

Accordingly, one object of the present invention is to provide a knot tier that is easy to use, and its associated method of use can be easily taught to surgeons.

Another object of the present invention is to provide a knot tier that is capable of generating the desired tension in the loop portion of the knot.

Yet another object of the present invention is to provide a knot tier that is capable of locking a sliding knot while the knot is held under the desired tension.

A further object of the present invention is to provide a method of knot tying such that reversing half-hitches on alternating posts are applied without having to re-thread the knot tier.

Still other objects of the present invention will be obvious to persons skilled in the art in view of this document.

SUMMARY OF THE INVENTION

These and other objects are achieved by the provision and use of the present invention, which comprises an apparatus and method for tying secure knots under a desired tension at a desired location remote from the entry portals. The invention provides a knot tier that is easy to use, with a method that may be readily taught to surgeons. The invention provides a knot tier which is capable of locking a sliding knot while the knot is held under a desired tension. The present method provides for securing knots with reversing half-hitches on alternating posts that are applied without having to re-thread the knot tier. The present invention also provides improved elements and processes for the purposes described above which are inexpensive, dependable and effective in accomplishing its intended purposes.

In one form of the invention, a knot tier is provided which comprises first guide means for slidingly advancing the knot along the post limb and for tensioning the loop portion of the knot to a desired level of tension by applying traction on the post limb, and second guide means proximate to the first guide means for aligning the wrapping limb against a snagging means intermediate the first and second guide means. Traction on the wrapping limb causes the shoulder of the wrapping limb to abut against the snagging means. With the shoulder of the wrapping limb trapped against the snagging means, the initially straight post limb is urged into a bend as traction is gradually released on the post limb while continued traction is applied to the wrapping limb. Distortion of the post limb locks the sliding knot. Further reversing half-hitches on alternating posts may be applied to further secure the knot.

In one preferred form of the invention, the knot tier's first and second guide means are located at the distal end(s) of the slender shaft(s) of the knot tier. The guide means can be located on a single shaft or on separate shafts of the knot tier. If the guide means are located on separate shafts, the guide means are in close proximity to each other during the tensioning and locking of the knot.

The first and second guide means can be of a variety of configurations including, but not limited to, an aperture, the opening of a bore, a slot, or any combination thereof. Preferably the first guide means is an aperture or the opening of a bore, and the second guide means is a slot. The snagging means can be in the form of a sharp edge, or a protuberance, intermediate the first and second guide means. The shoulder of a sliding knot is snagged against the snagging means when traction is applied on the wrapping limb (through the second guide means) so as to pull the knot towards the second guide means.

Alternatively, the sharp edge of the entrance of the first or second guide means can also constitute a snagging means. The shoulder of a sliding knot is snagged against the sharp edge of the entrance when traction is applied on the wrapping limb (through the second guide means) so as to pull the knot towards the second guide means.

The opening of the second guide means itself can also constitute snagging means if the narrowest width is between one and three times the diameter of the suture. In this case, traction on the wrapping limb pulls the knot against the opening of the second guide means. As most sliding knots have a gross diameter of greater to or equal to three times the width of the suture, the knot is "snagged" against the entrance to the second guide means.

The knot tier generally works best with a proximal locking sliding knot but will also works with a distal locking sliding knot.

Although the knot tier does not distort the post limb of the non-locking sliding knot, traction of the wrapping limb against the snagging means or the entrance of the second guide means will tighten the wrappings around the post and thereby increase the resistance to backing off by the sliding knot. Thus, the present invention also has significant utility with non-locking sliding knots.

One preferred embodiment of the knot tier comprises a slender cylindrical shaft; a handle at the proximal end of shaft in the form of a ring sized to fit the thumb of the user; first guide means located at the distal end of the shaft, wherein the first guide means comprises an aperture; second guide means located at the distal end of the shaft, wherein the second guide means comprises two legs in close proximity to the first guide means, the legs angled distally; and snagging means, wherein the snagging means comprise the crotch of the two legs and the entrance to the second guide means defined by the two legs.

BRIEF DESCRIPTION OF THE DRAWINGS

Still other objects and features of the present invention will be more fully disclosed or rendered obvious by the following detailed description of the preferred embodiments of the invention, which are to be considered together with the accompanying drawings wherein like parts are referred to by like numbers and letters and further wherein:

FIGS. 17–22 are schematic views showing the knot tier of FIGS. 14–16 advancing, tightening and locking a sliding knot;

FIGS. 23–32 are schematic views showing further details of the knot advancing, tightening and locking process shown in FIGS. 17–22;

FIGS. 42–46 are successive partial, lateral cross-sectional views showing the embodiment of FIGS. 36–40 engaging and locking a sliding knot;

DETAIL DESCRIPTION OF THE PREFERRED EMBODIMENTS

Figure 1:
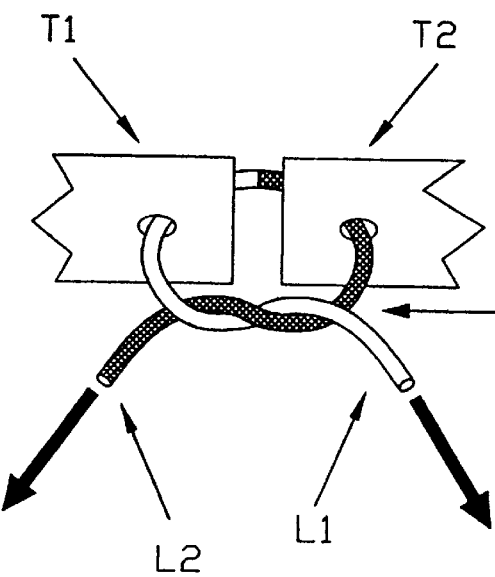
FIG. 1 is a plan view of a knot with a symmetrical throw.
Figure 2:
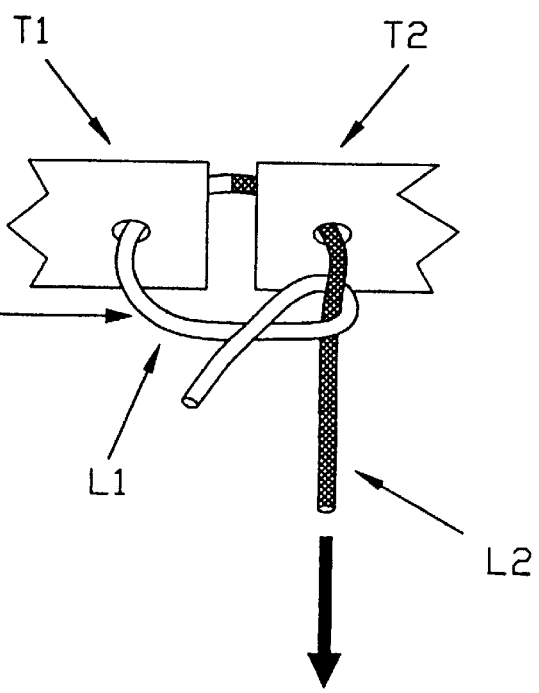
FIG. 2 is a plan view of the knot of FIG. 1, transformed into an over-under half-hitch.
Figure 3:
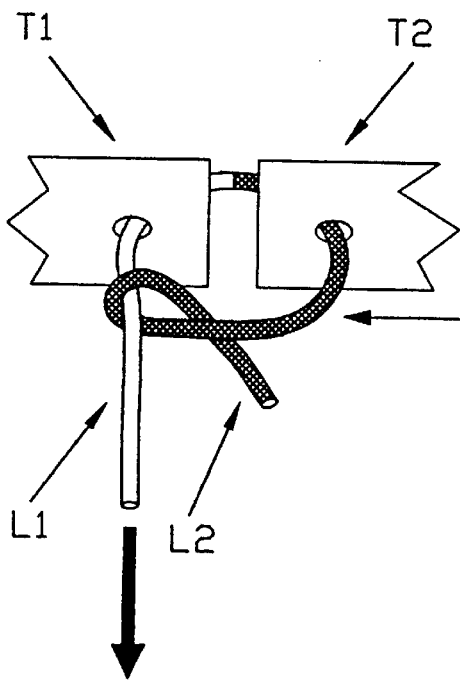
FIG. 3 is a plan view of the knot of FIG. 1, transformed into an under-over half-hitch.
Figure 4:
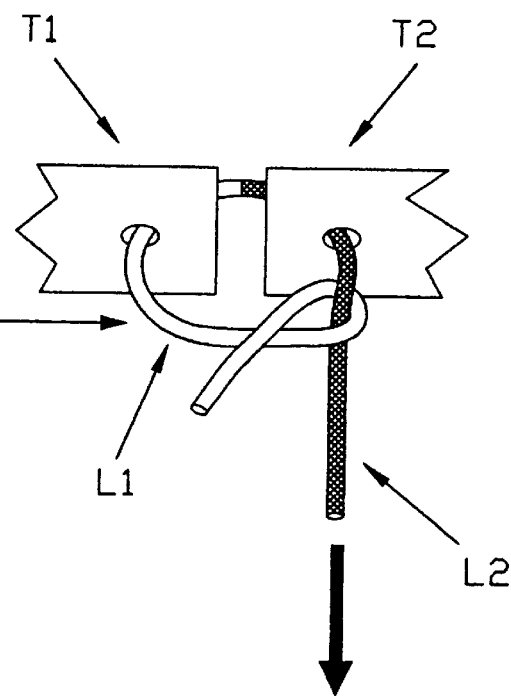
FIG. 4 is a plan view of the knot of FIG. 3, transformed into an over-under half-hitch.
Figure 5:
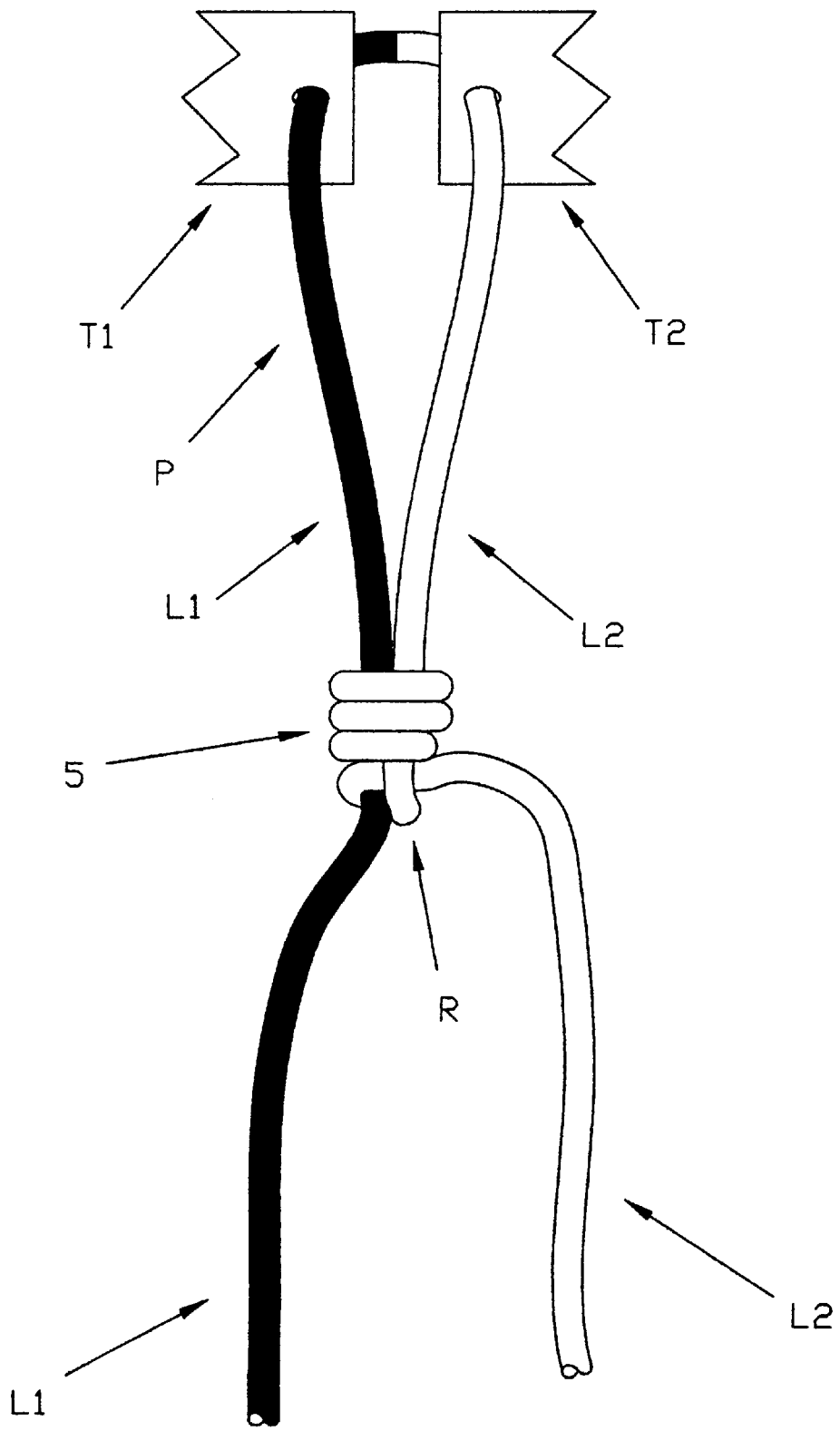
FIG. 5 is a plan view of a generic sliding knot.
Figure 6:
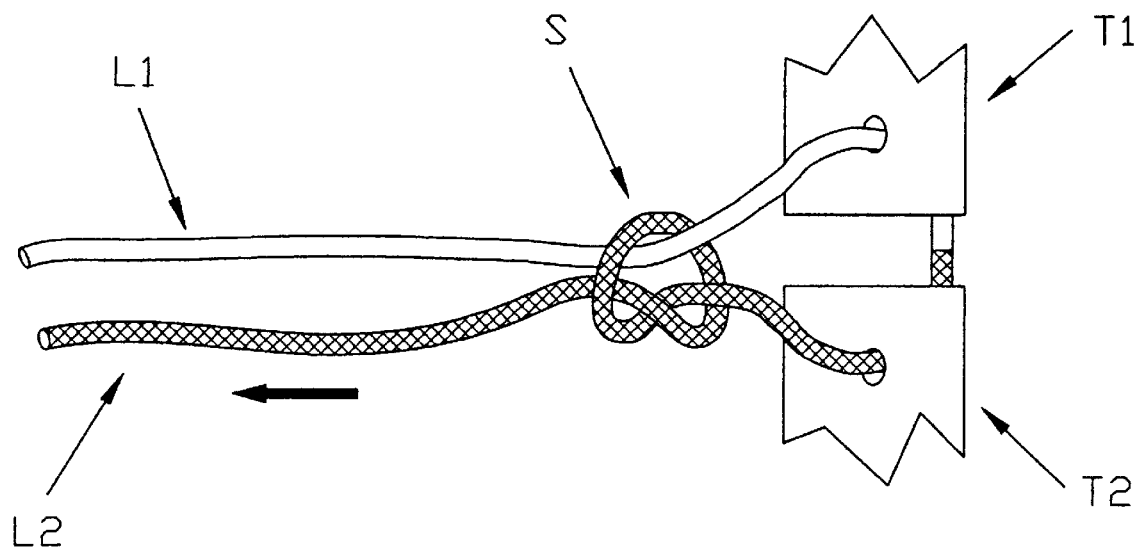
FIG. 6 is a plan view of a non-locking overhand throw sliding knot.
Figure 7:
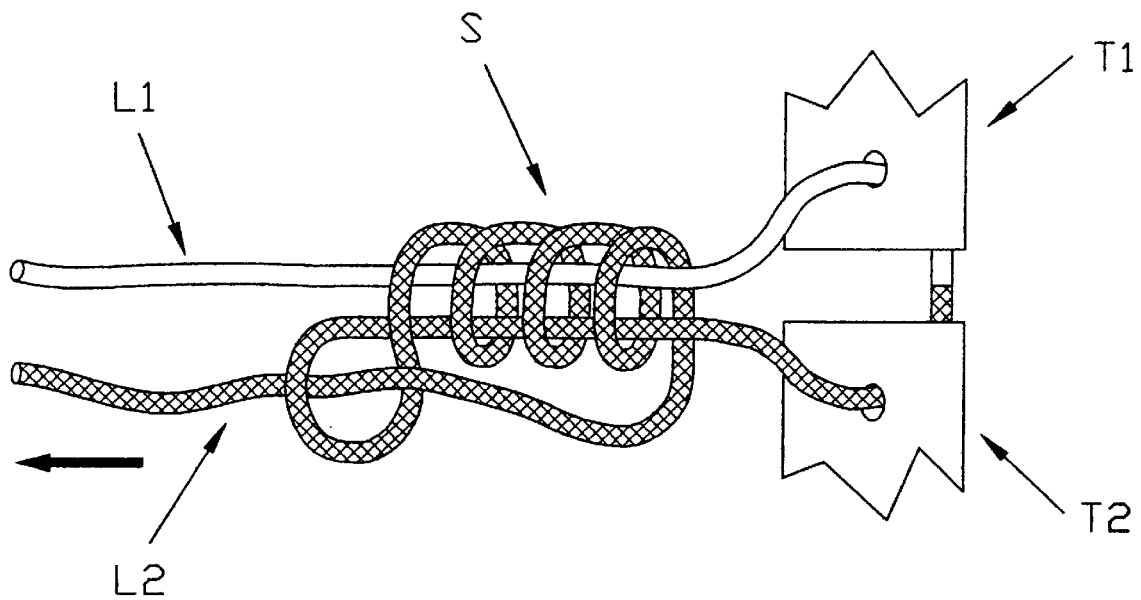
FIG. 7 is a plan view of a non-locking modified Duncan loop sliding knot.
Figure 8:
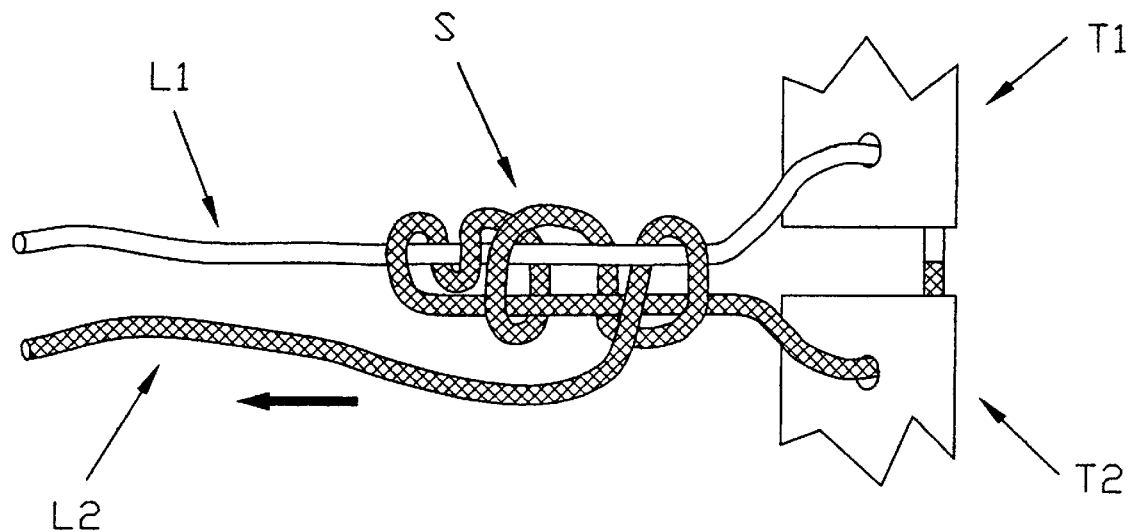
FIG. 8 is a plan view of a distal-locking Roeder sliding knot.
Figure 9:
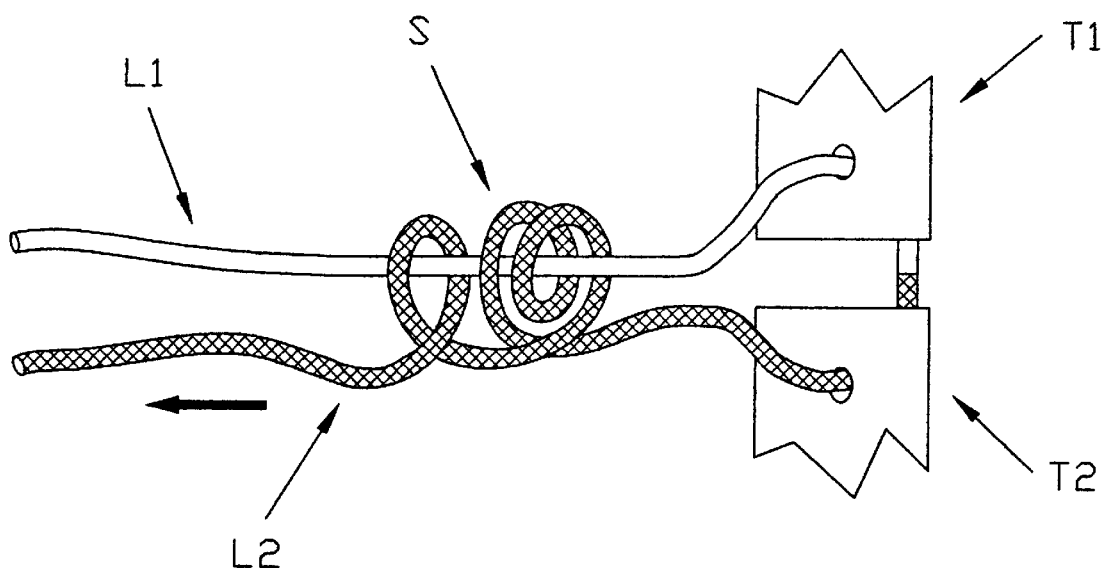
FIG. 9 is a plan view of a proximal-locking tautline hitch sliding knot.
Figure 10:
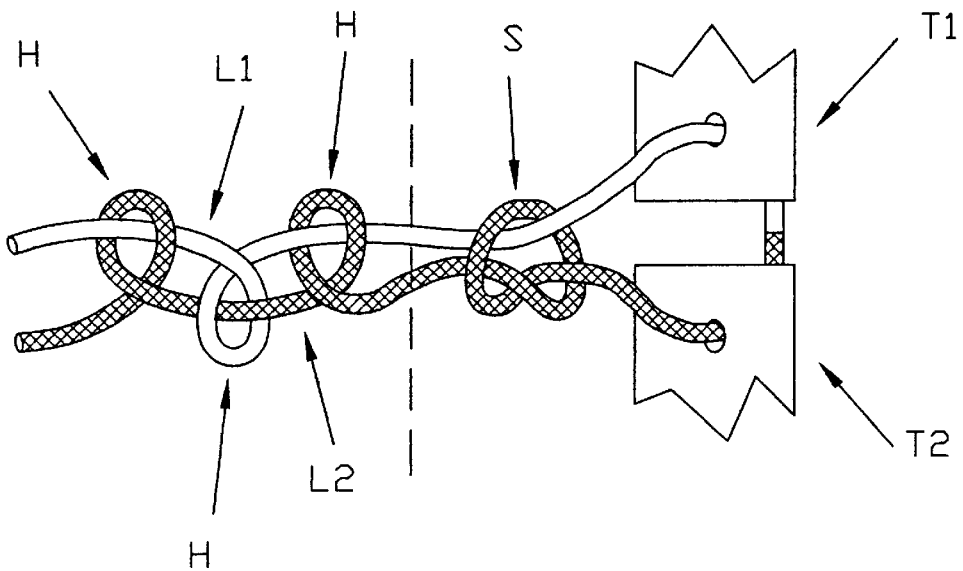
FIG. 10 is a plan view of a non-locking overhand throw sliding knot with additional reversing half-hitches on alternating posts.
Figure 11:
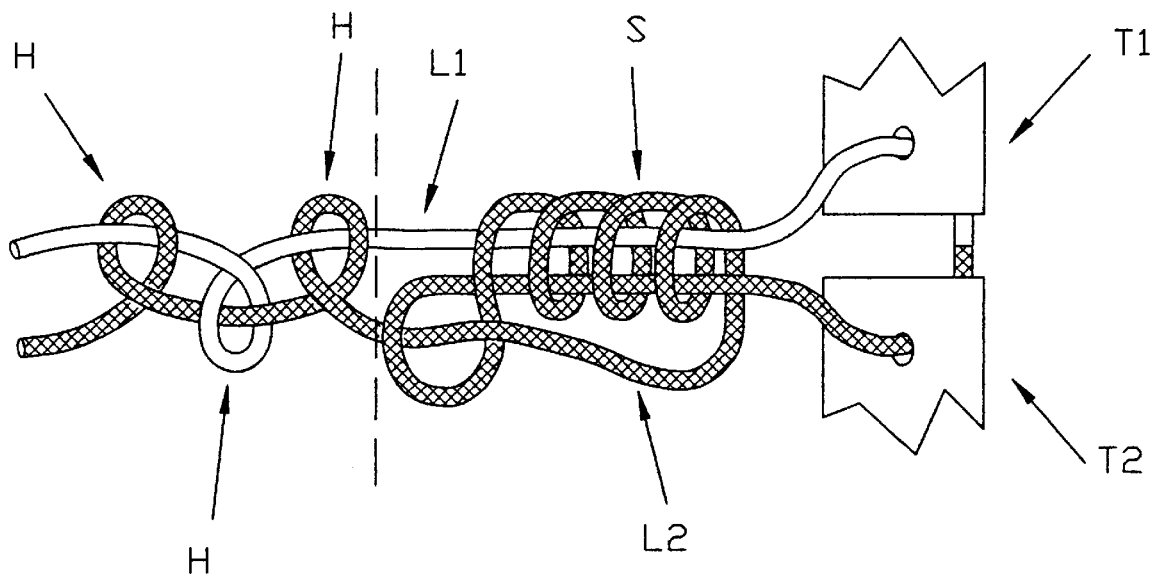
FIG. 11 is a plan view of a non-locking modified Duncan loop sliding knot with additional reversing half-hitches on alternating posts.
Figure 12:
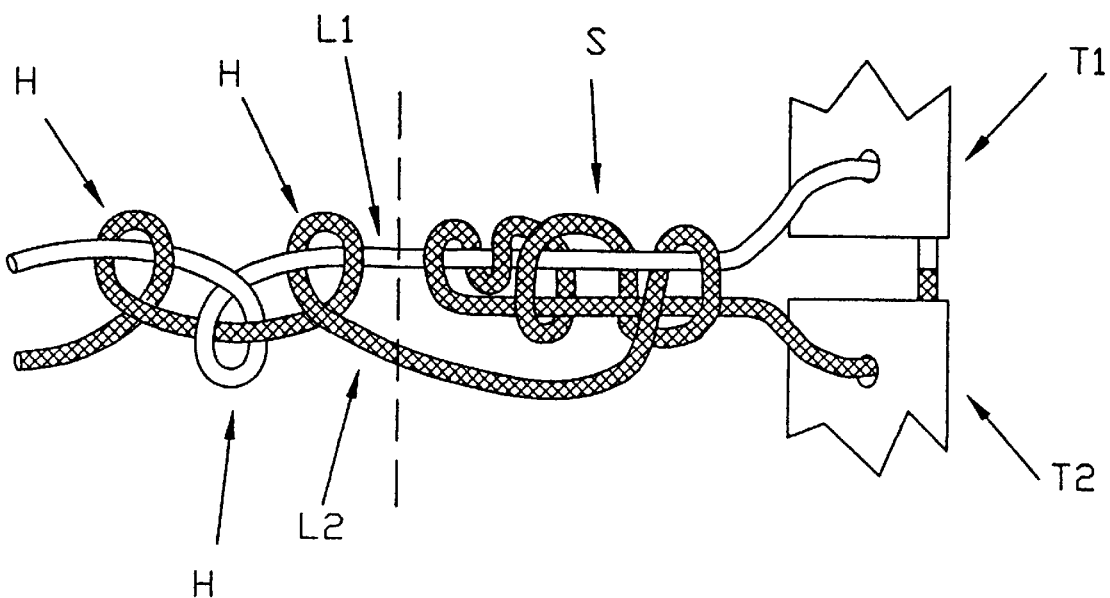
FIG. 12 is a plan view of a distal-locking Roeder sliding knot with additional reversing half-hitches on alternating posts.
Figure 13:
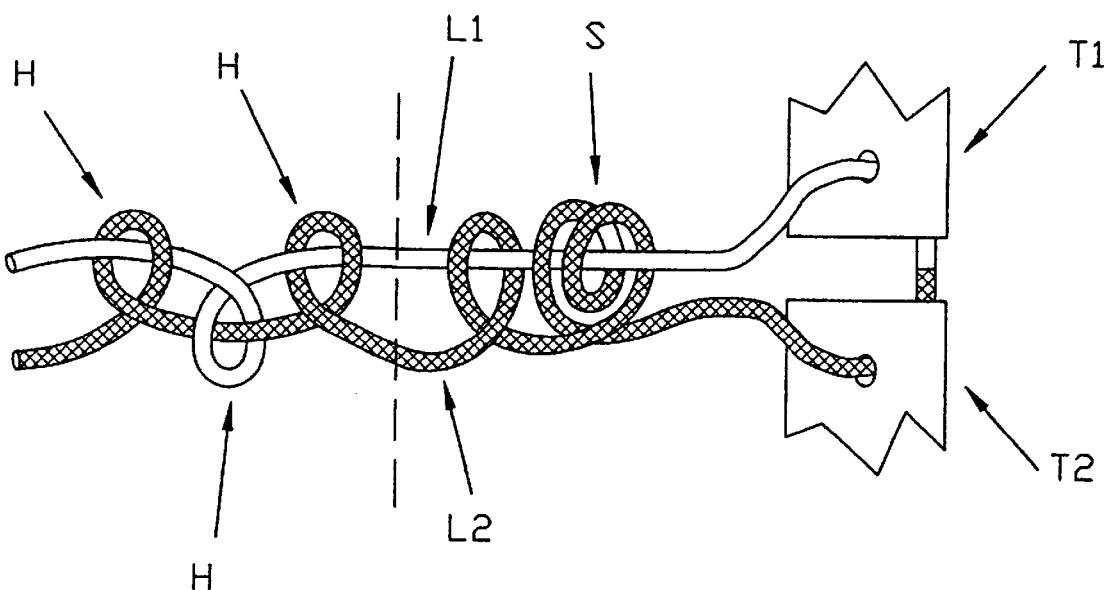
FIG. 13 is a plan view of a proximal-locking tautline hitch sliding knot with additional reversing half-hitches on alternating posts.
Figure 14:
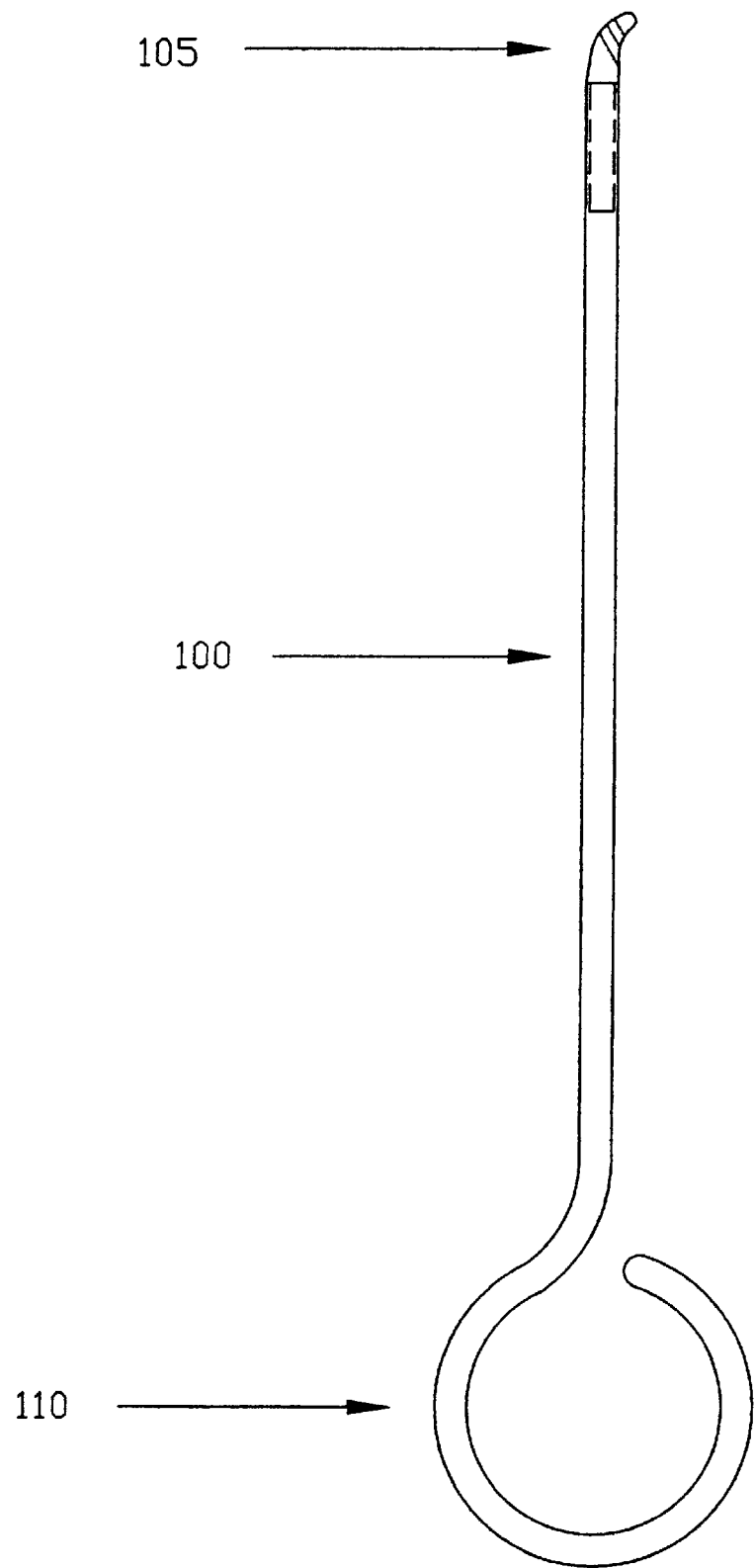
FIG. 14 is a side elevational view of an embodiment of a knot tier constructed in accordance with the present invention.
Figure 16:
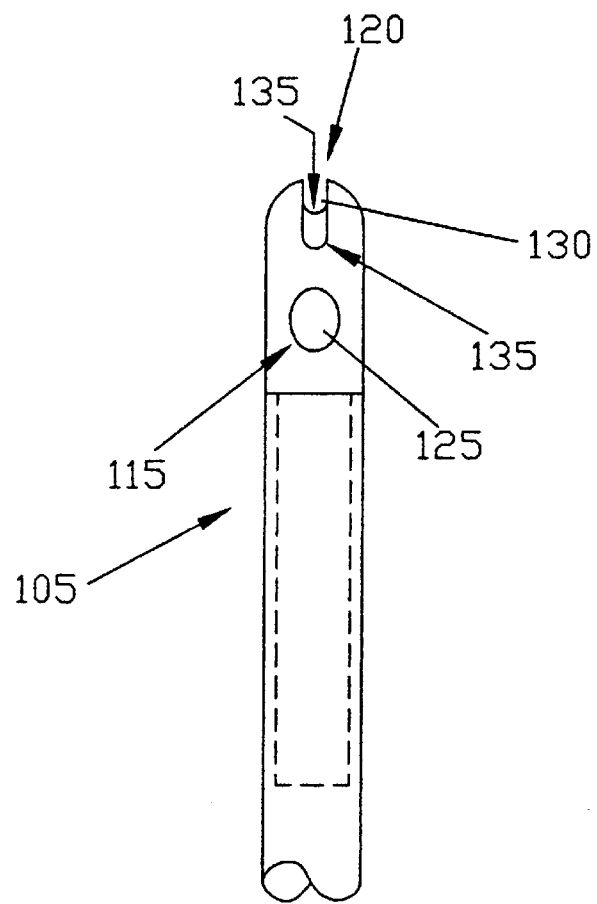
FIG. 16 is a partial front elevational view, drawn to an enlarged scale, of the embodiment of FIG. 14.
Figure 15:
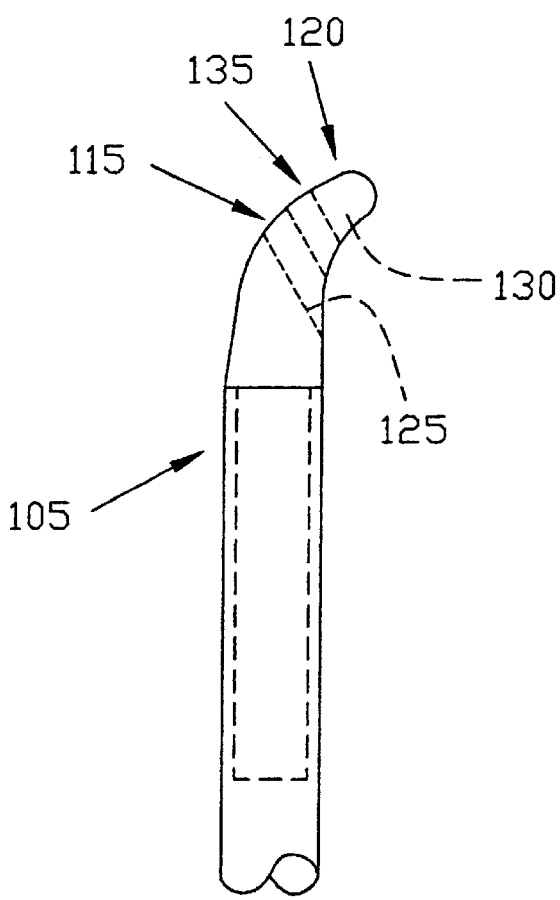
FIG. 15 is a partial side elevational view, drawn to an enlarged scale, of the embodiment of FIG. 14.

FIGS. 14–16 show a novel knot tier formed in accordance with the present invention. FIGS. 17–22 and FIGS. 23–32 show the advancing, tightening and locking of a sliding knot using the knot tier of FIGS. 14–16. The knot shown in these drawings is meant to represent a generic sliding knot and does not correspond to a particular sliding knot (although in a preferred embodiment of the invention the sliding knot comprises a proximal locking sliding knot). FIGS. 17–22 represent close-up views of the distal end of the knot tier during the knot tying sequence, whereas FIGS. 23–32 illustrate environmental views of the surgical area during the knot tying sequence.

The objectives of the surgical technique are:

1. Tighten a sliding knot (preferably a proximal locking knot) to a desired tension against the tissue to be repaired.
2. Lock the primary sliding knot prior to switching post.
3. Apply reversing half-hitches on alternating posts to complete the locking of the primary sliding knot.

Looking now at FIGS. 14–16, there is shown a knot tier 100 which comprises a preferred form of the invention. Knot tier 100 comprises a distal end 105 and a proximal end 110.

First guide means 115 and second guide means 120 are formed at the distal end of knot tier 100. In a preferred form of the invention, first guide means 115 comprise a bore 125, and second guide means 120 comprise a slot 130. Snagging means 135 are formed at the distal end of knot tier 100, intermediate first guide means 115 and second guide means 120. Snagging means 135 may comprise the lower edge of the entrance of slot 130 (i.e., the edge of the entrance of the slot that is nearest to bore 125), and the entrance of the slot itself (i.e., the width of the slot is smaller than the width of the knot, therefore the knot cannot be pulled into the slot).

The distal end 105 of knot tier 100 is preferably formed out of plastic so as to avoid damaging the suture during advancing, tightening and locking of the sliding knot, and particularly when the sliding knot is pulled against the snagging means 135.

Looking next at FIGS. 17–22 and 23–32, knot tier 100 is intended to be used as follows.

Figures 17, 18:
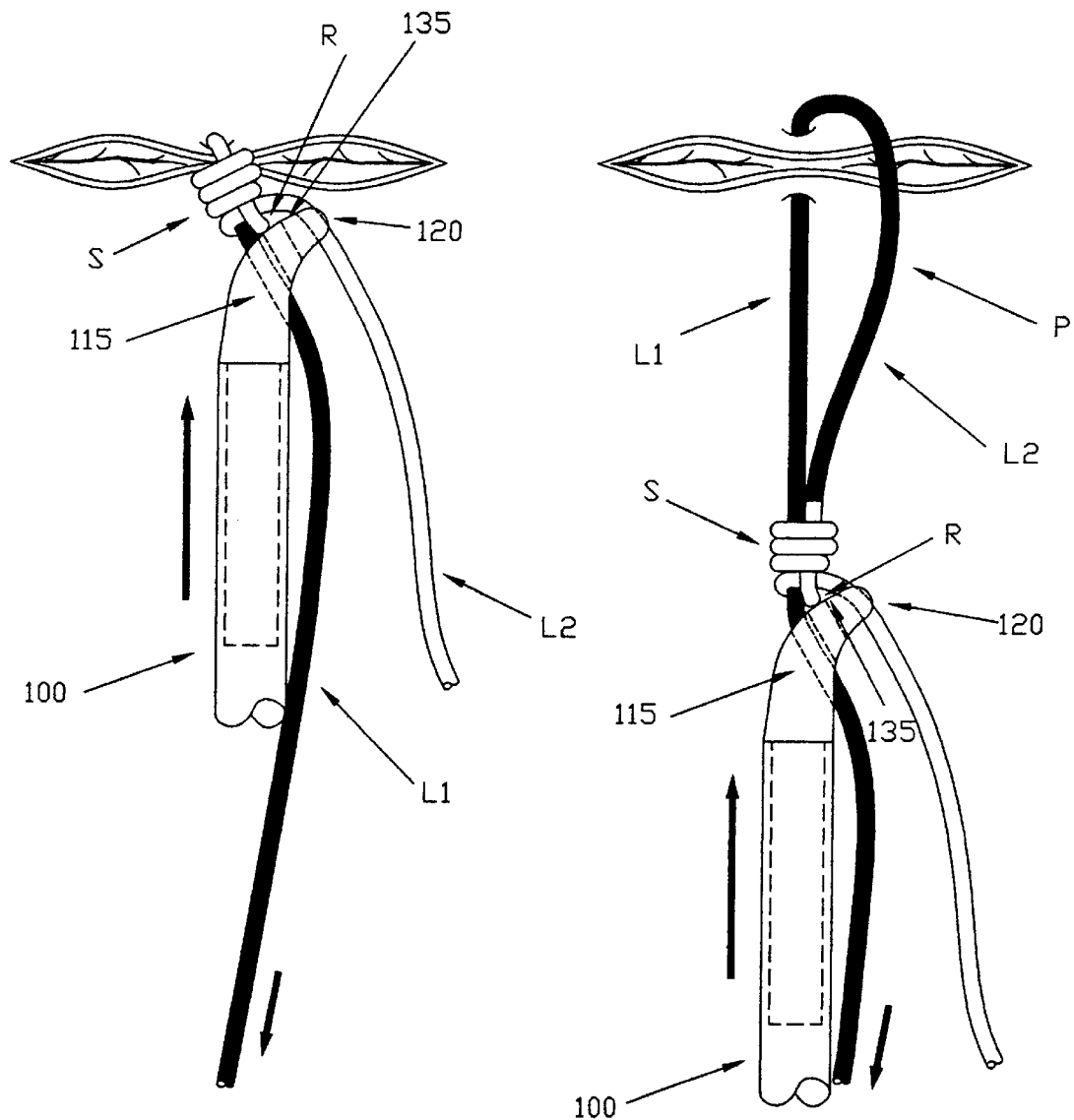
Figure 22:
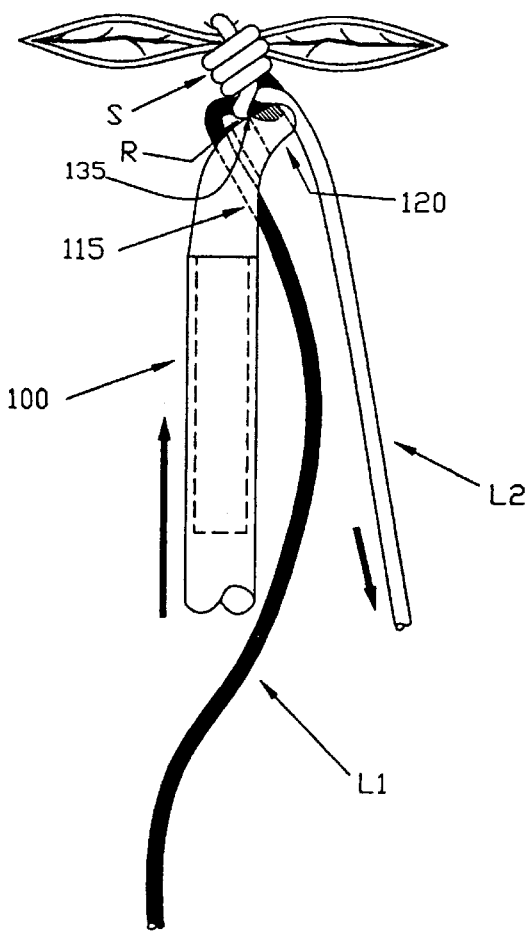
Figure 21:
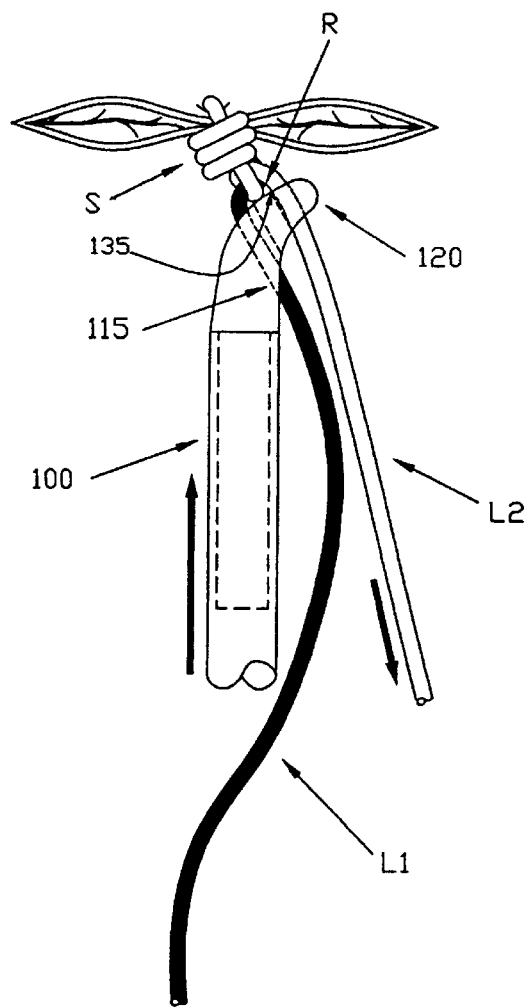
Figure 23:
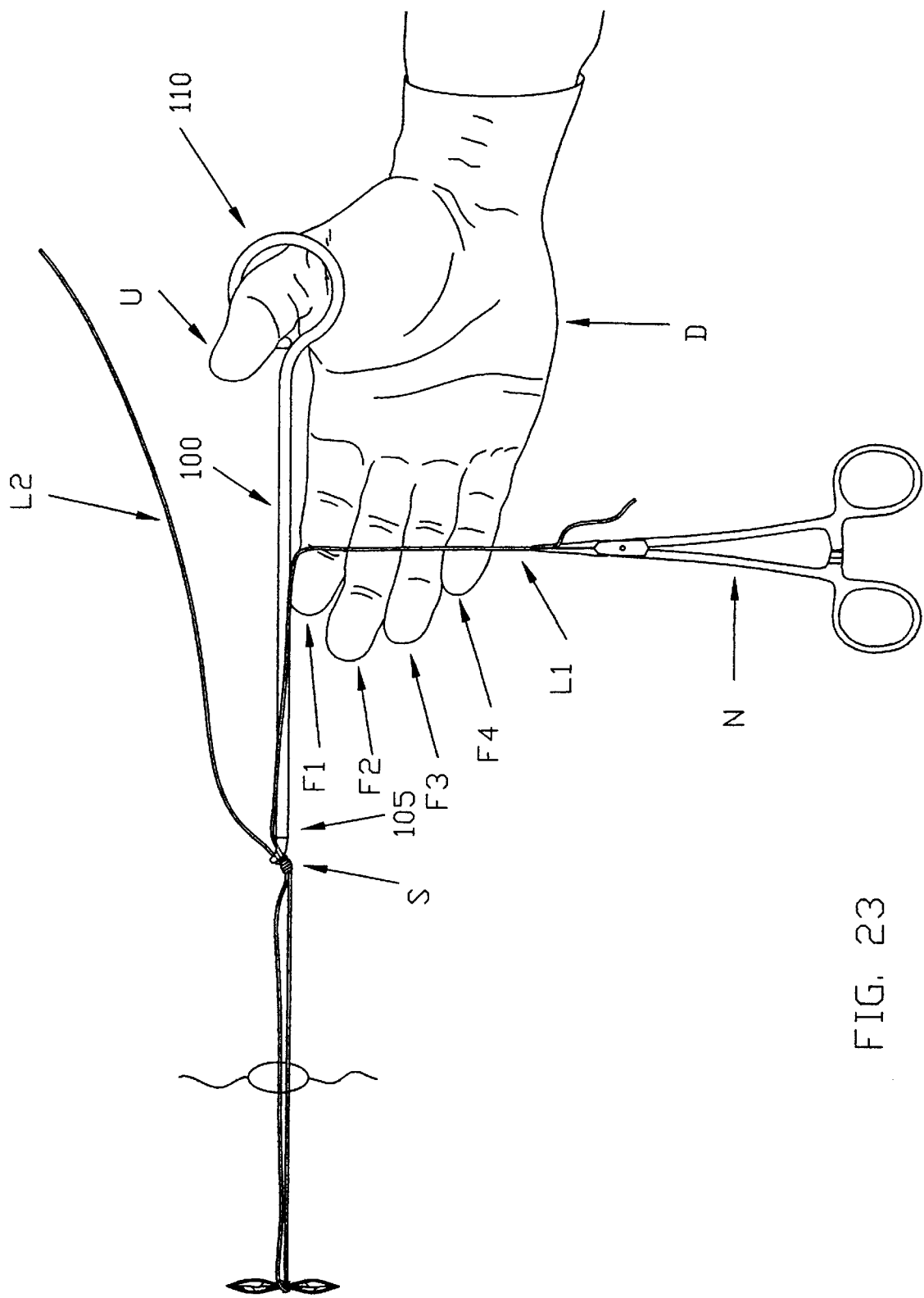
Figure 24:
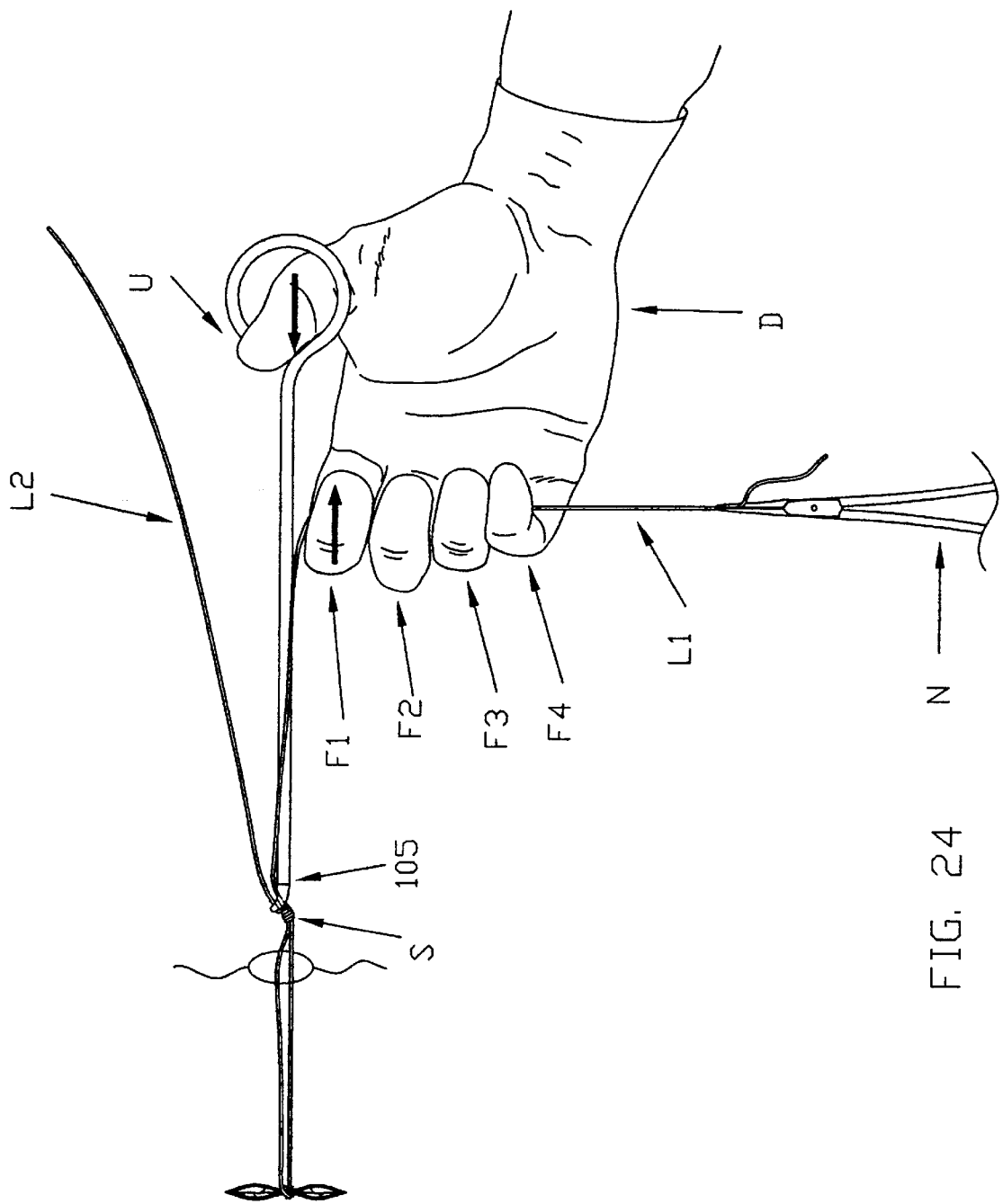
Figure 25:
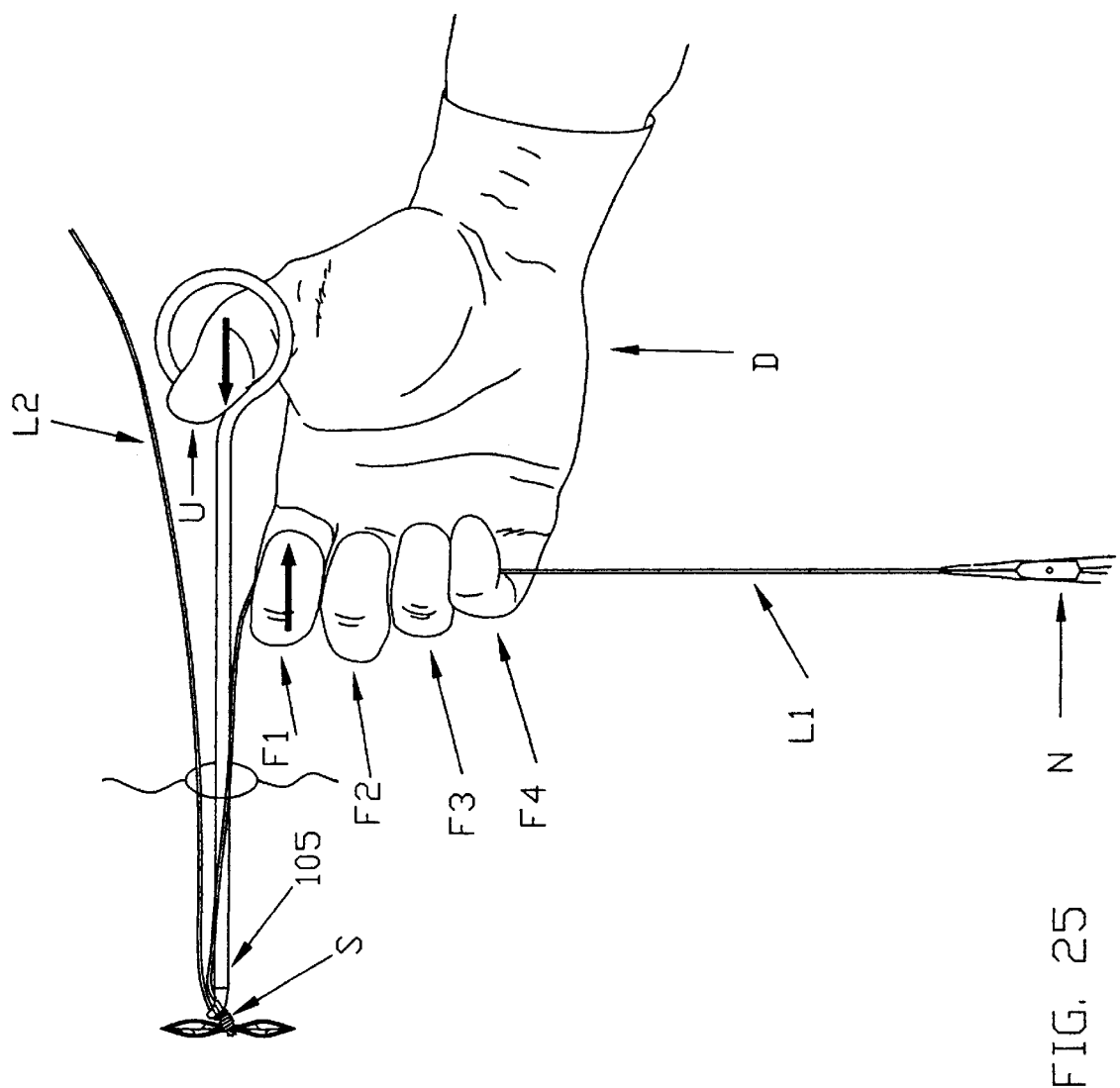
Figure 26:
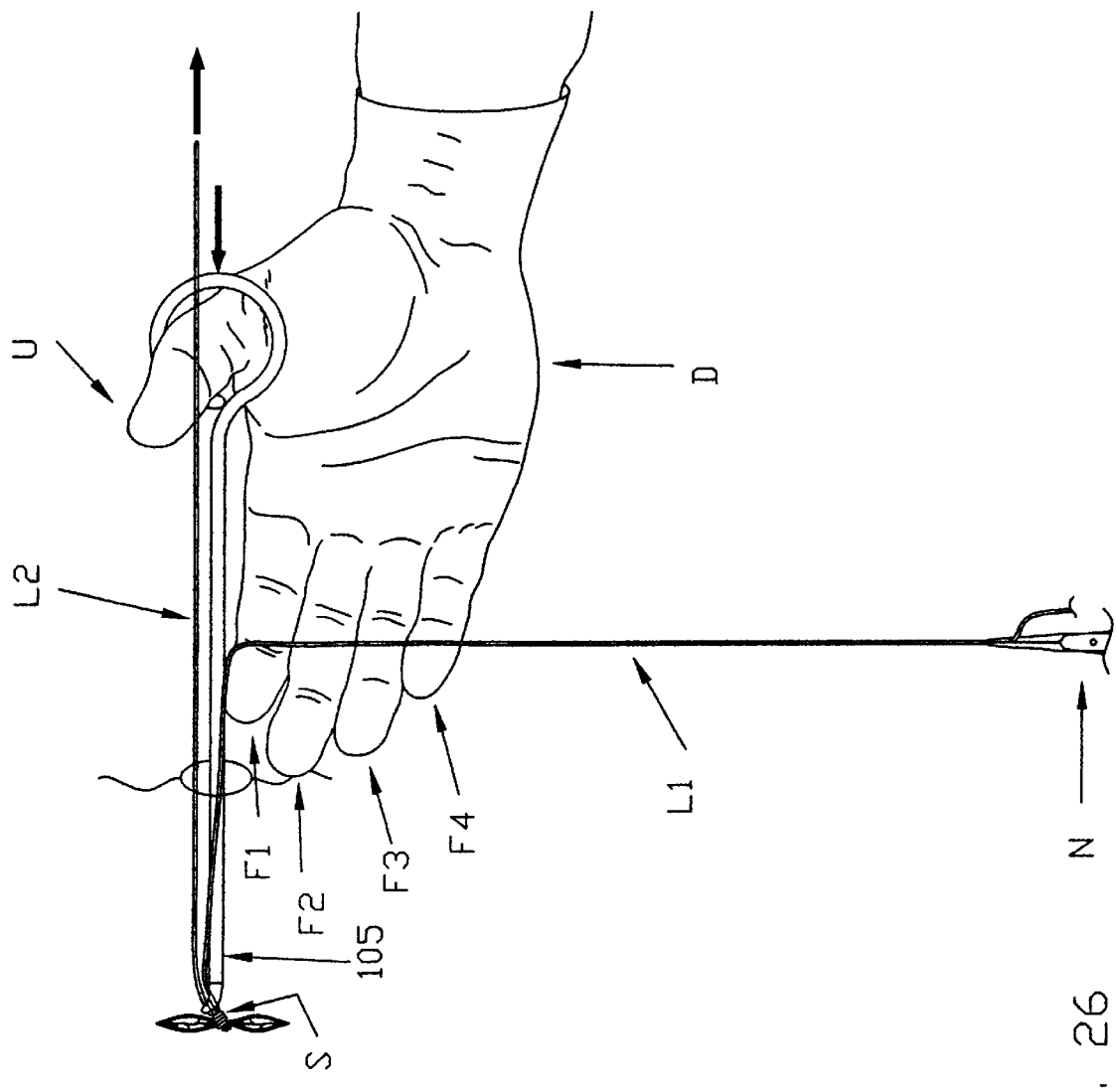
Figure 29:
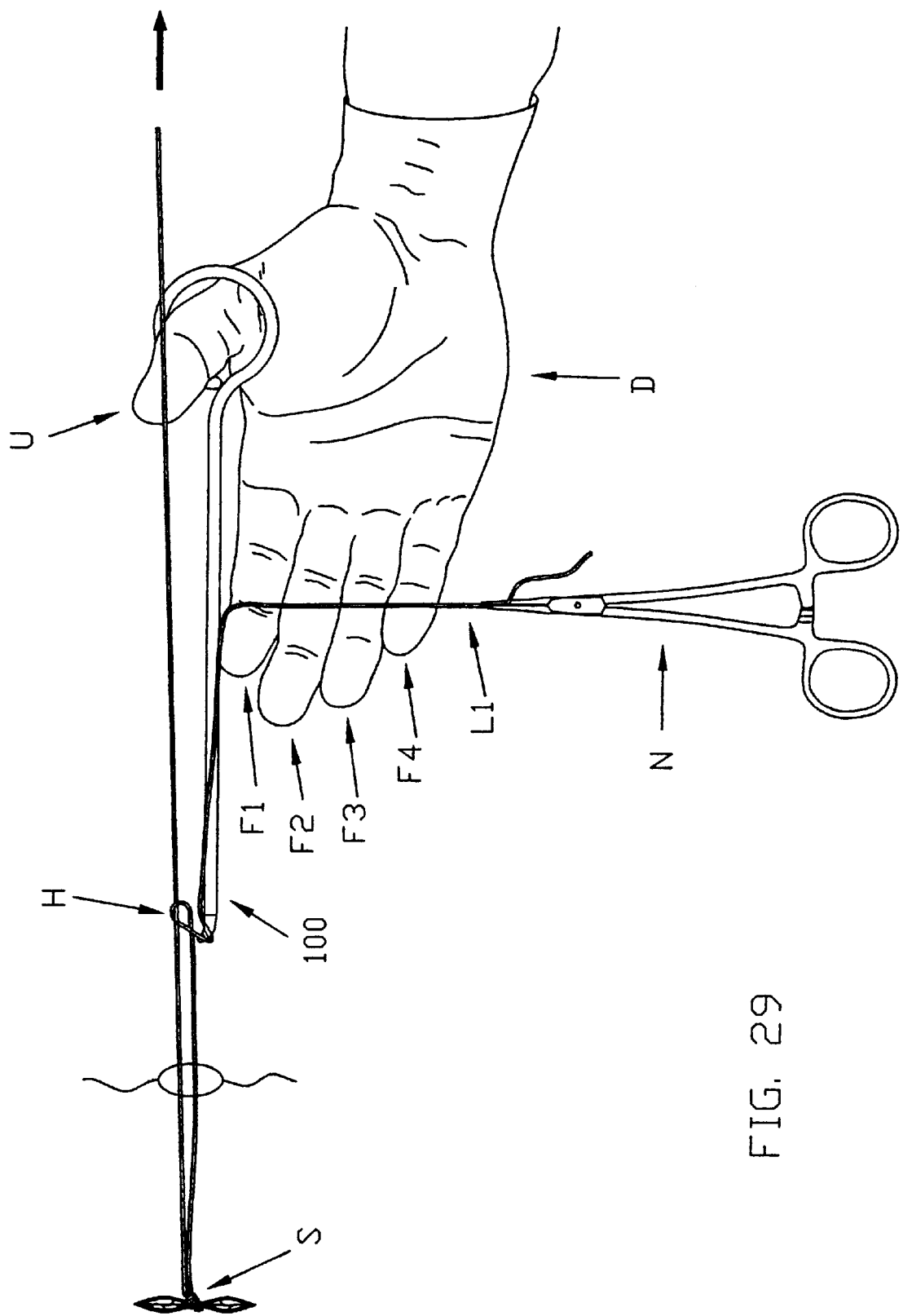
Figure 30:
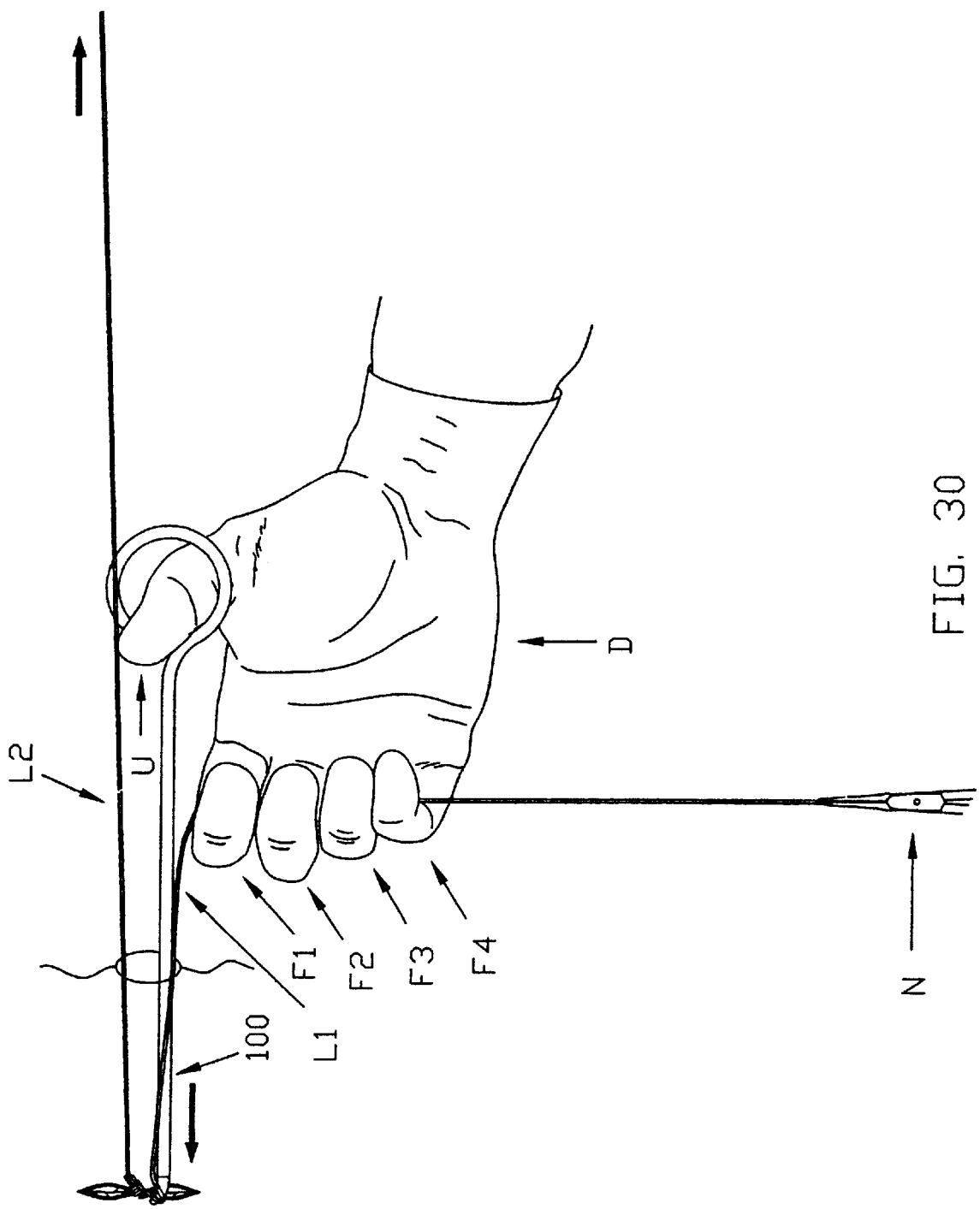
Figure 31:
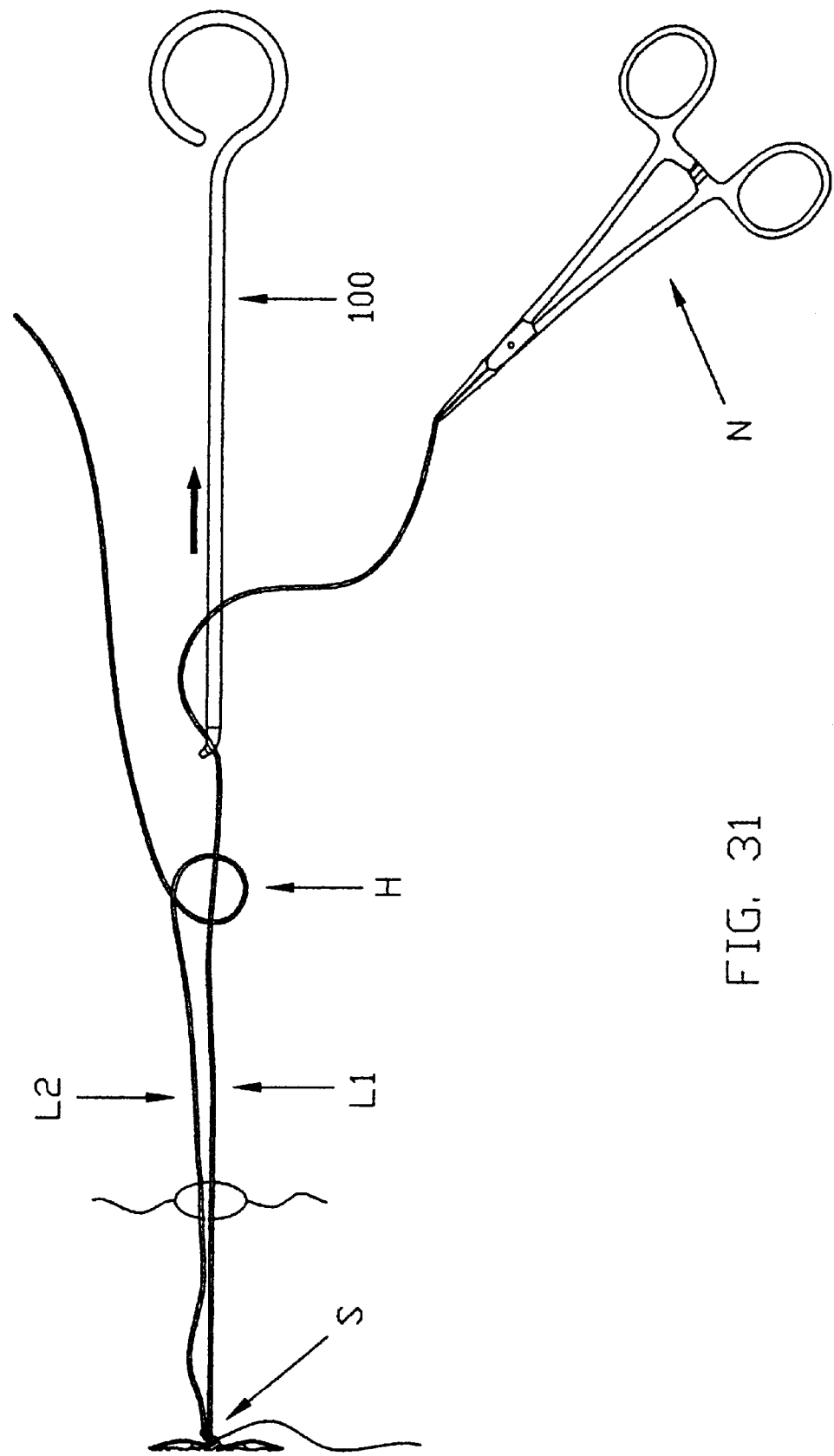
Figure 32:
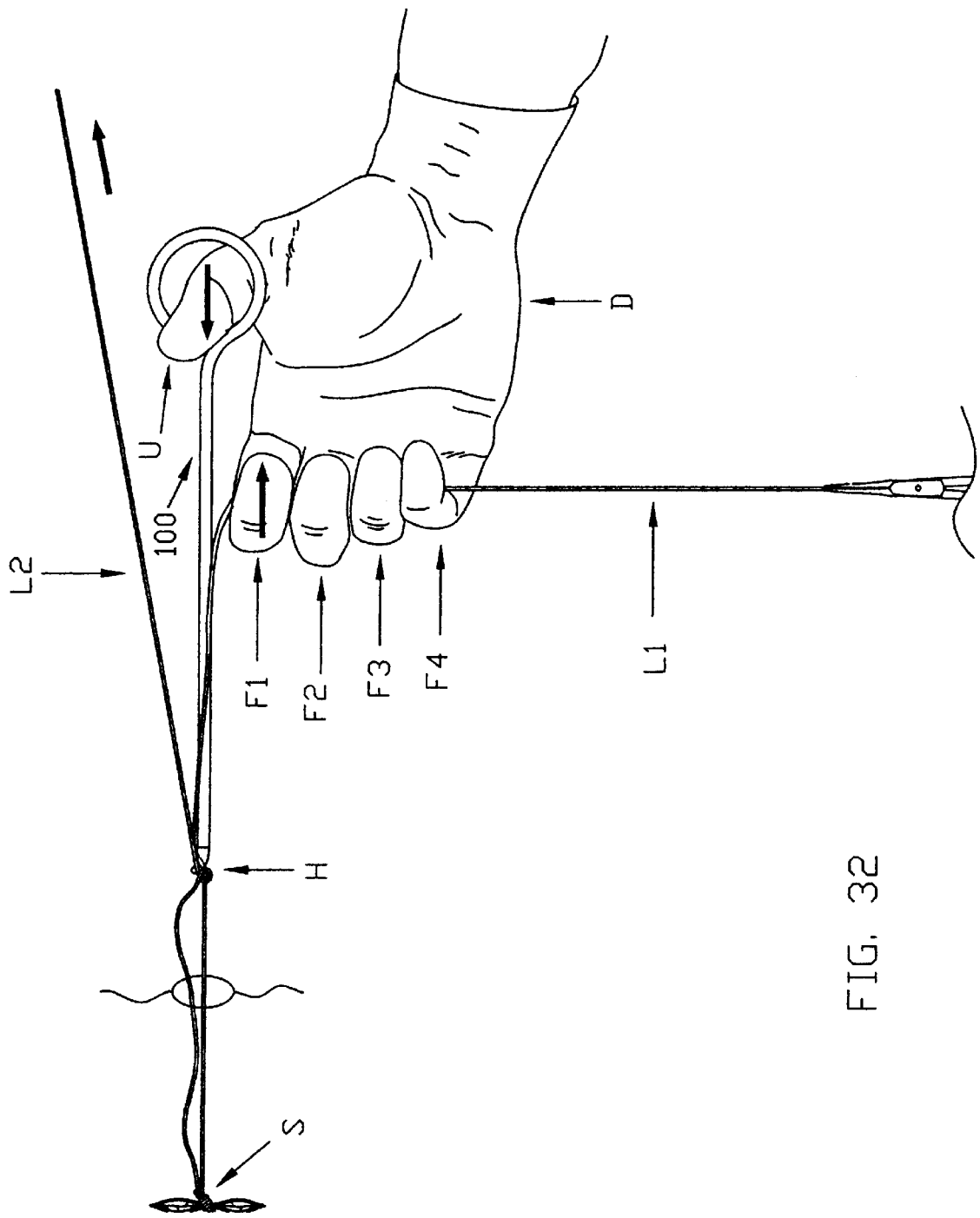

1. The powder on the glove of the surgeon's hand D is cleaned off and the glove is then dried. This improves the traction between the suture and the glove enhancing suture manipulation.
2. Tie a sliding knot S (preferably a proximal locking knot) extracorporeally. Thread the post limb L1 through the aperture 125 of the knot tier and attach a snap N to the end of the suture limb L1 as a deadweight. Hold the knot tier 100 in the right hand with the thumb U through the proximal loop handle of the knot tier. The post limb L1 is draped over the distal crease of the index finger F1. Seating of the second limb (i.e., the wrapping limb) L2 of the suture inside the slot 130 of the knot tier is not critical at this point in the procedure.
3. Grip the post limb L1 of the suture by flexing (i.e., curling) the fingers F1–F4 (FIG. 24). By further flexing (i.e., curling) the fingers F1–F4 and pushing the loop handle of the knot tier forward, the sliding knot S is advanced along the post limb L1. When the fingers F1–F4 are re-extended, the slack of the post limb L1 around the fingers F1–F4 is taken up by the weight of the snap N. The post limb L1 is again gripped by the flexed fingers F1–F4 and the knot S is advanced farther by again flexing (i.e., curling) the fingers F1–F4 and pushing the loop handle of the knot tier 100 forward. Therefore, by alternately flexing (i.e., curling) and extending the fingers F1–F4 and pushing the loop handle forward with the thumb U, the sliding knot S is progressively advanced forward and into the joint (FIGS. 17 and 24). This technique of advancing a sliding knot is analogous to a ratchet mechanism.
4. When the sliding knot S is about 1 centimeter from the tissue, the tip 105 of the knot tier 100 is manipulated to capture the wrapping limb L2 within the slot 130. When the sliding knot S abuts against the tissue, the tissue margins are urged into coaptation by tensioning the loop P of the sliding knot S (FIGS. 17 and 18). Then the post limb L1 is gripped with the flexed fingers F1–F4. The tension in the suture loop P is then increased by pulling the post limb L1 and pushing the knot tier 100 against the sliding knot S (FIGS. 18 and 25).
5. Traction is then applied to the wrapping limb (i.e., the second limb) L2 while the tension in the loop P is maintained by continuing tension on the post limb (i.e., the first limb) L1, as shown in FIG. 19. Tension is maintained on the wrapping limb (i.e., the second limb) L2 as the post limb (i.e., the first limb) L1 is gradually released (FIGS. 20 and FIG. 26). Then the tension in the wrapping limb L2 is increased to distort the post limb L1 (FIG. 21). Further increases in the tension of the wrapping limb L2 will cause further distortion of the first limb L1. This comes about because the shoulder R of the proximal locking knot S is snagged against the lower edge of the entrance of the slot 130, i.e., because it is snagged against the snagging means 135. The width of this slot 130 (being between 1.0 to 3.0 times the size of the width of the suture) allows part of the distorted first limb L1 to be drawn into the slot 130, further increasing the distortion of the first limb L1 (FIG. 22). This distortion of the first limb L1 prevents the sliding knot S from backing off while further half-hitches H are applied.
6. The knot tier 100 is then withdrawn from the joint. Traction is applied to the second limb L2 to prevent unlocking of the sliding knot S as the knot tier 100 is withdrawn from the joint. The first limb L1 is left threaded through the aperture 125 of the knot tier 100 and the snap N is left attached to the first limb L1. The second limb L2 is wrapped around the first limb L1 (FIG. 27) to form a first half-hitch H (under-over, with the first limb L1 as the post limb, as shown in FIG. 27). The half-hitch H is then fully flipped so that the second limb L2 then becomes the post limb by pulling on the second limb L2 and moving the tip 105 of the knot tier 100 distally and away from the second limb L2 (FIGS. 27 and 28). There are two reasons for flipping the knot S so to cause the second limb L2 to become the post limb. First, as the first half-hitch H is advanced, tension is maintained on the second limb L2, which will prevent the locked sliding knot S from unlocking. Second, it is easier to "pull" a half-hitch forward (FIG. 29) than to "push" a half-hitch forward (if the half-hitch is not flipped as depicted in FIGS. 27 and 28, where the half-hitch is formed with the first limb L1 acting as the post limb, and where the post limb is also threaded through the knot tier, the knot tier has to "push" the half-hitch so as to advance it).
7. The first half-hitch H is "pulled" (FIG. 29) into the joint by alternately flexing (i.e., curling) and extending the fingers F1–F4 with the same "ratchet" action as previously described for the primary sliding knot S.
8. When the first half-hitch H is snuggled up against the primary sliding knot S, it is further tightened by a "past pointing" technique (FIG. 30). The tip of the knot tier 100 is positioned past the knot S, the first limb L1 is gripped with the flexed (i.e., curled) fingers F1–F4, and the knot tier 100 is pushed forward. At the same time, the second limb L2 is pulled so as to tighten the first half-hitch H.
9. The next step is to tie a second half-hitch H (i.e., a reversed half-hitch on the opposite post). See FIG. 31. Since the first half-hitch H was tightened down with the second limb L2 as the post limb, the second half-hitch H is to be tightened down with the first limb L1 as the post limb. FIG. 31 shows that the knot tier 100 has been withdrawn from the joint. The second limb L2 is wrapped around the first limb L1 from an "under-over" direction so as to form the desired half-hitch H with the first limb L1 as the post limb.
10. FIG. 32 illustrates one way of advancing the second half-hitch H into the joint by "pushing" the half-hitch H ahead of the tip 105 of the knot tier 100. The half-hitch H is advanced in small steps by the ratchet motions created by the flexing (i.e., curling) and extending of fingers F1–F4. For each small advancement, the suture of the second limb L2 ahead of the second half-hitch H "bunches" up. This slack is taken up by pulling on the proximal end of the second limb L2. The second half-hitch H is then advanced by another small increment.

11. When the second half-hitch is pressed up against the first half-hitch, the past pointing technique as described above in Step 8 is used to tighten the knot.

12. As mentioned previously, it is often easier to "pull" a half-hitch forward rather than to "push" it forward. As an alternative to "pushing" the half-hitch forward as described in Step 10, the knot may be "pulled" into the joint until it is close to the tissue and then the knot is pushed along the final segment of the advancement. As described in Step 6, this "pulling" is accomplished by first fully flipping the half-hitch by transforming the configuration as shown in FIG. 27 to the configuration as shown in FIG. 28, with the second limb L2 as the post limb. As described in Step 7 for the first half-hitch, the second half-hitch is then pulled into the joint until it is about one centimeter from the previous half-hitch. Tension is then released on the second limb L2, while increased tension is applied to the first limb L1 by flexing the fingers F1–F4 and pushing the knot tier's loop handle forward at the same time. This will cause the second half-hitch to be fully flipped back into the starting configuration with the first limb L1 as the post limb. The second half-hitch is then advanced along the final one centimeter segment using the "pushing" technique as described in Step 10. The second half-hitch is finally tightened down by the past pointing technique, similar to that shown in FIG. 30.

Figure 33:
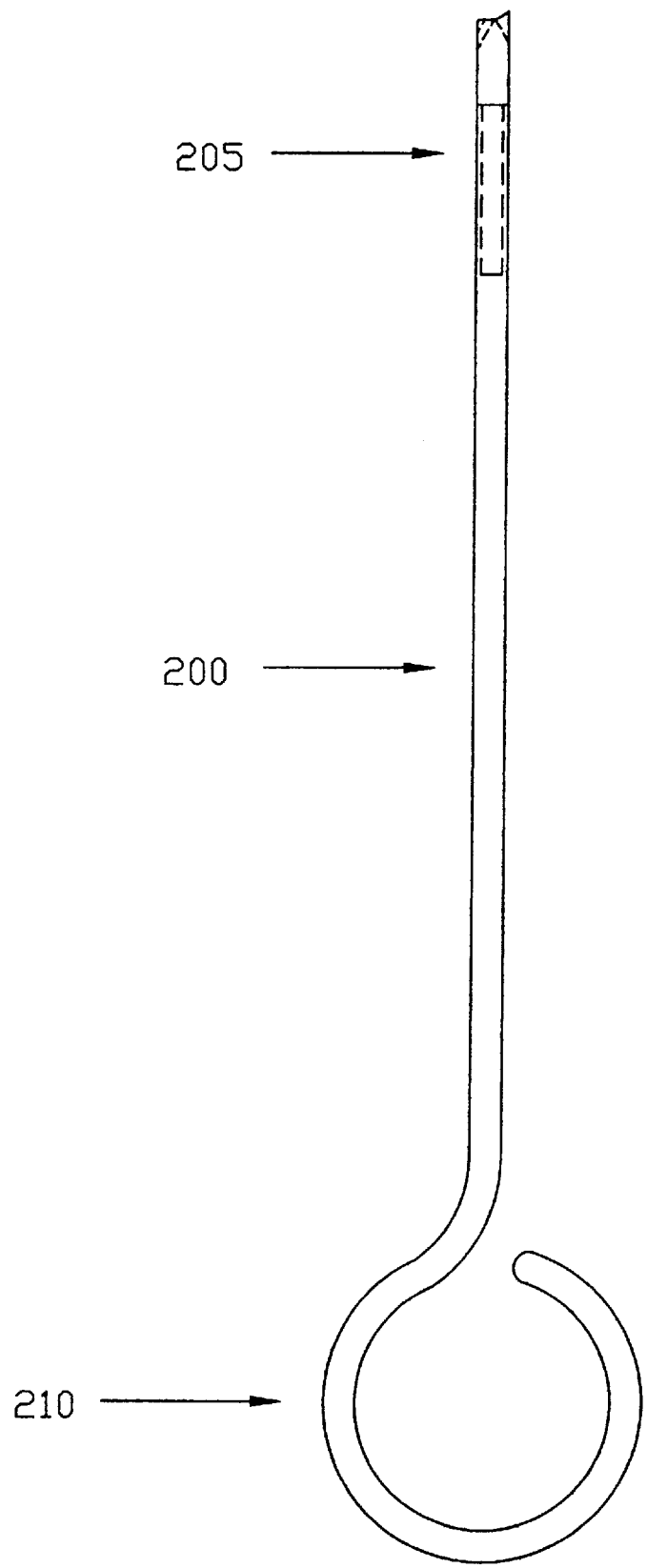
FIG. 33 is a side elevational view of another embodiment of knot tier formed in accordance with the present invention.
Figure 35:
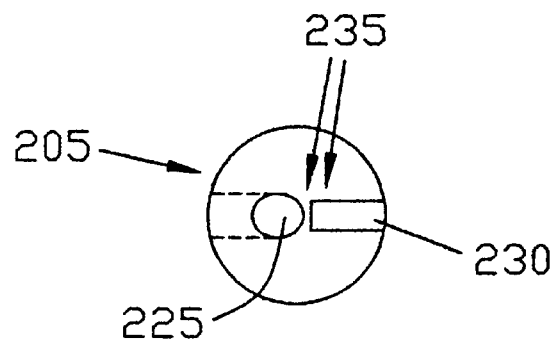
FIG. 35 is a partial plan view, drawn to an enlarged scale, of the embodiment of FIG. 33.
Figure 34:
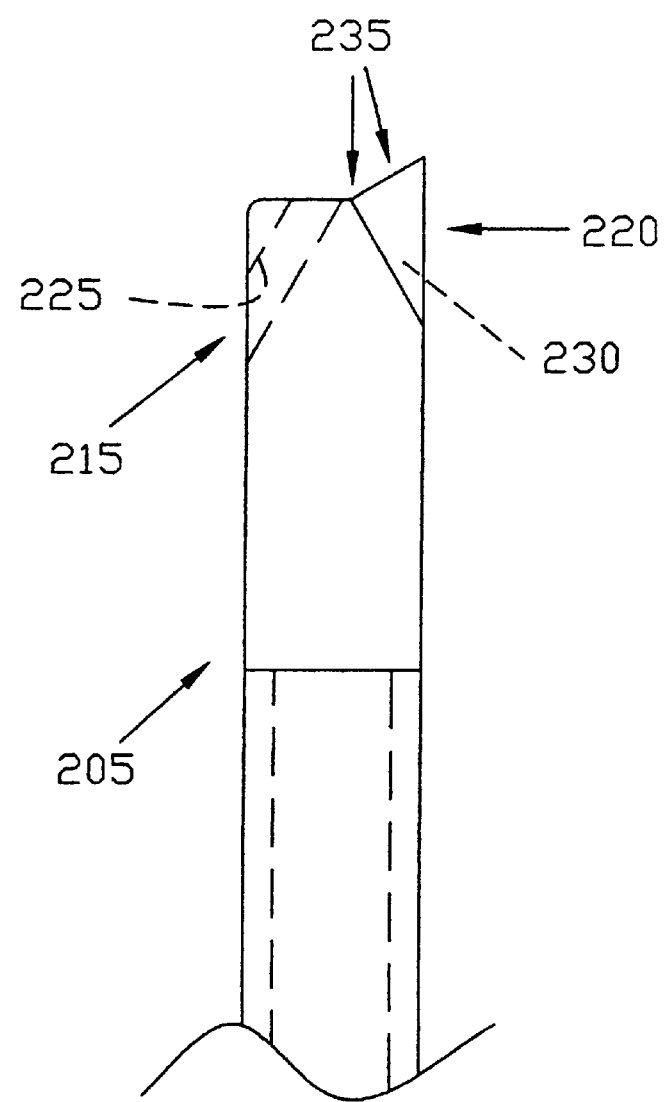
FIG. 34 is a partial side elevational view, drawn to an enlarged scale, of the embodiment of FIG. 33.
Figure 36:
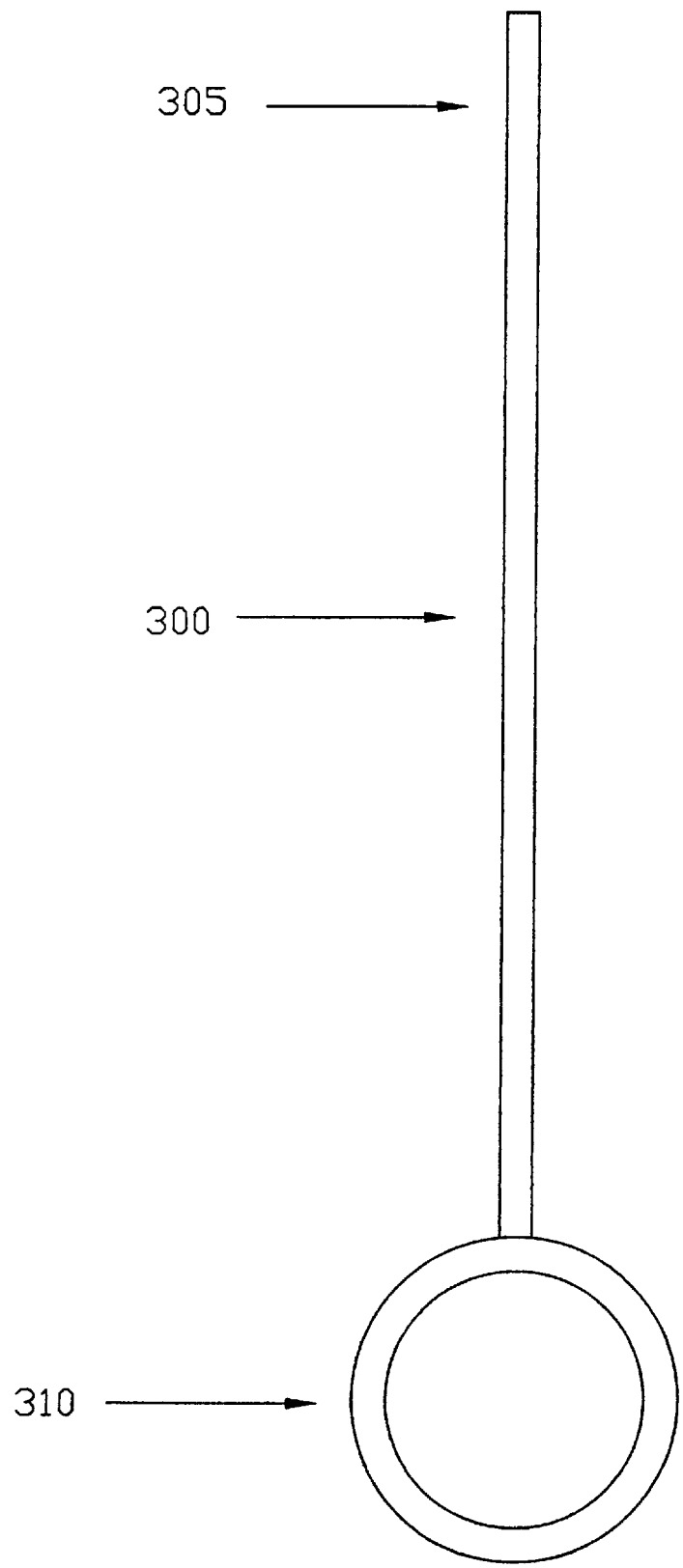
FIG. 36 is a side elevational view of a further embodiment of knot tier formed in accordance with the present invention.
Figure 37:
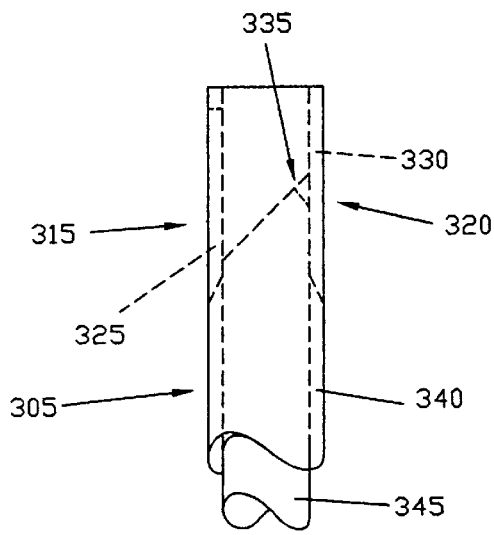
FIGS. 37 and 38 are partial side and front elevational views, respectively, drawn to an enlarged scale, of the embodiment of FIG. 36.
Figure 38:
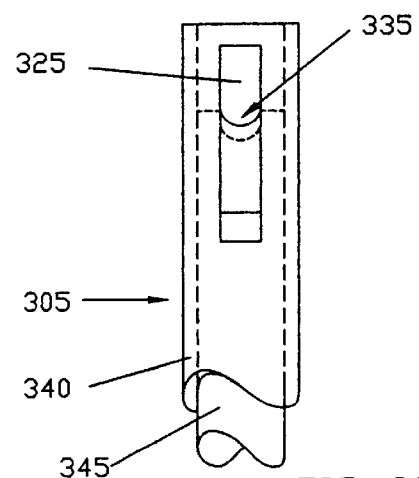
Figure 39:
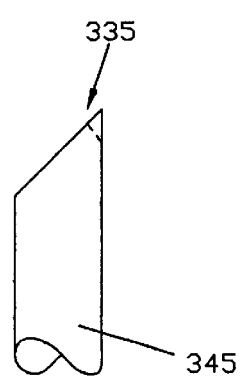
FIGS. 39 and 40 are partial side and front elevational views, respectively, drawn to an enlarged scale, of a core of the embodiment of FIGS. 37 and 38.
Figure 40:
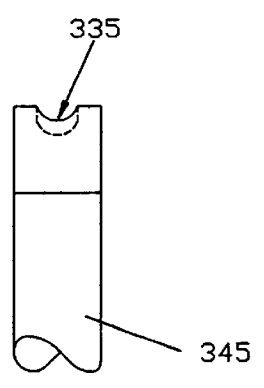

Looking next at FIGS. 33–35, there is shown a knot tier 200 also formed accordance with the present invention. Knot tier 200 comprises a distal end 205 and a proximal end 210. First guide means 215 and second guide means 220 are formed at the distal end of knot tier 200. In a preferred form of the invention, first guide means 215 comprise a bore 225, and second guide means 220 comprise a slot 230. Snagging means 235 are formed at the distal end of knot tier 200, intermediate first guide means 215 and second guide means 220. Snagging means 235 may comprise the lower edge of the entrance of slot 230 (i.e., the edge of the entrance of the slot that is nearest to bore 225), and the entrance of the slot itself (i.e., the width of the slot is smaller than the width of the knot, therefore the knot cannot be pulled into the slot).

The distal end 205 of knot tier 200 is preferably formed out of plastic so as to avoid damaging the suture during advancing, tightening and locking of the sliding knot, and particularly when the sliding knot is pulled against the snagging means 235.

Knot tier 200 is used in substantially the same way as knot tier 100 described above.

Figure 41:
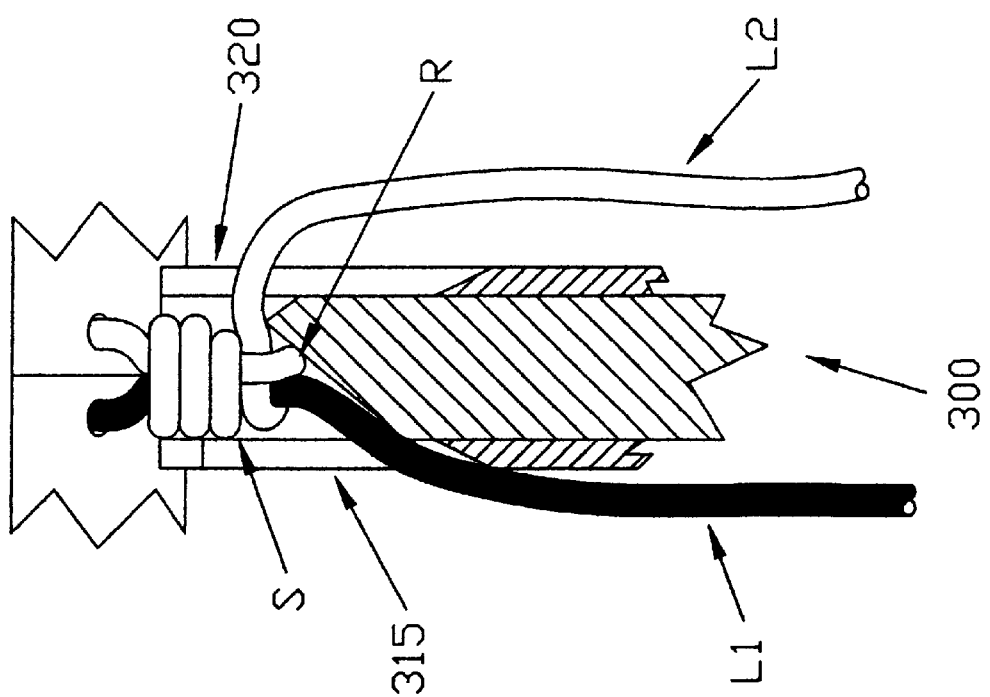
FIG. 41 is a partial, lateral cross-sectional view of the embodiment of FIGS. 36–40, engaged with a sliding knot.
Figure 42:
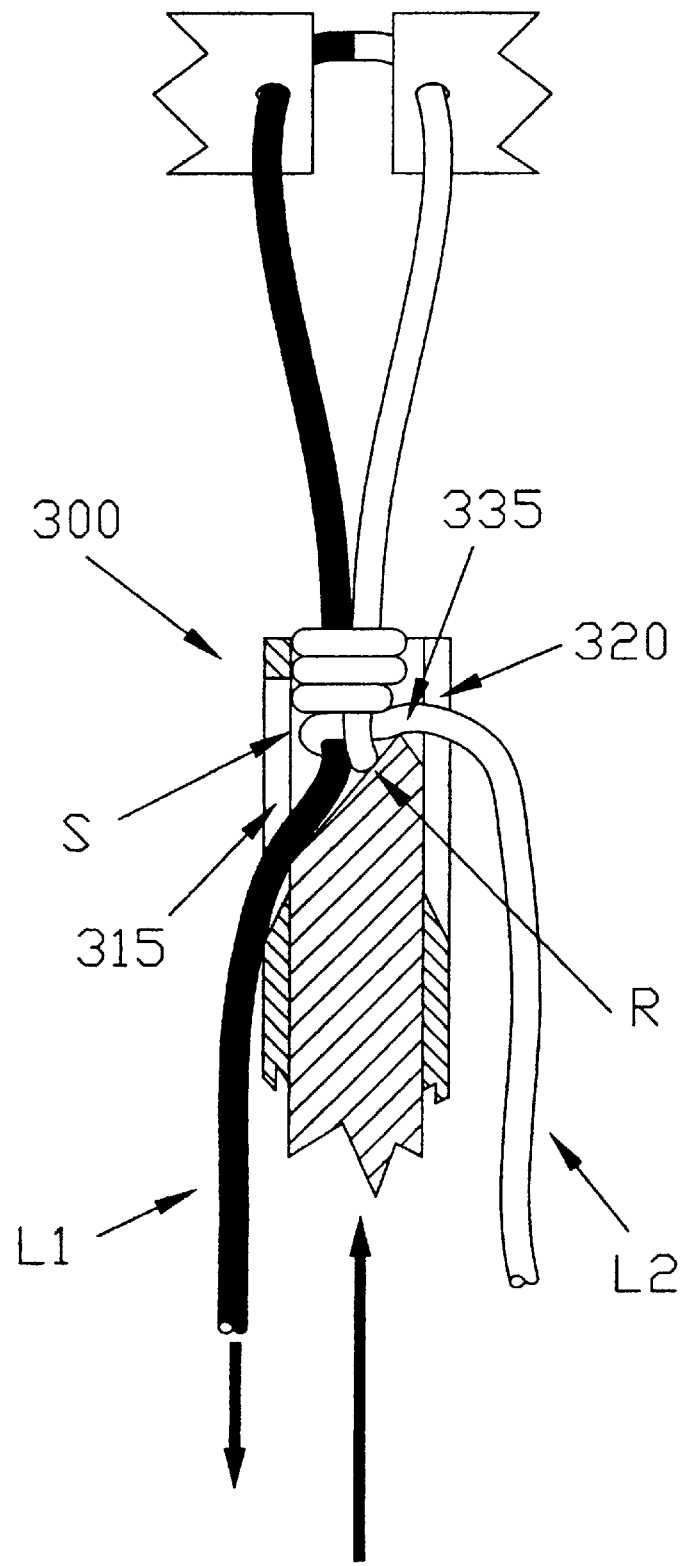
Figure 47:
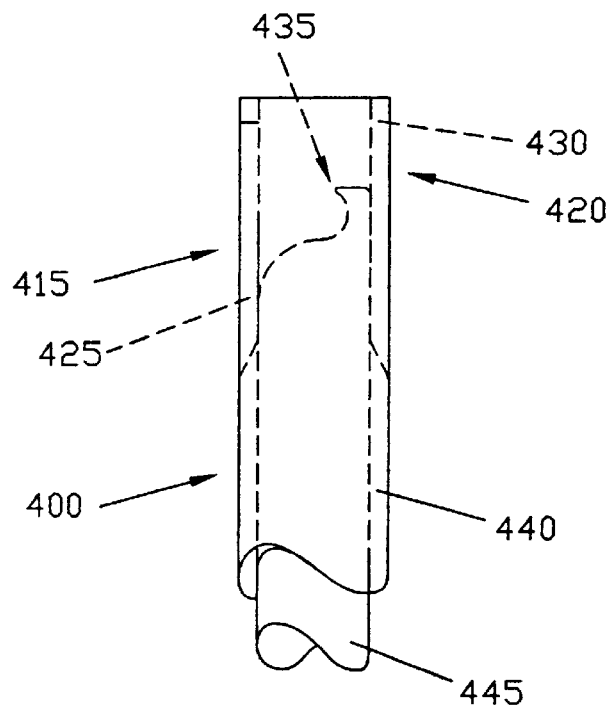
FIGS. 47 and 48 are partial side and front elevational views, respectively, drawn to an enlarged scale, of another embodiment of knot tier.
Figure 48:
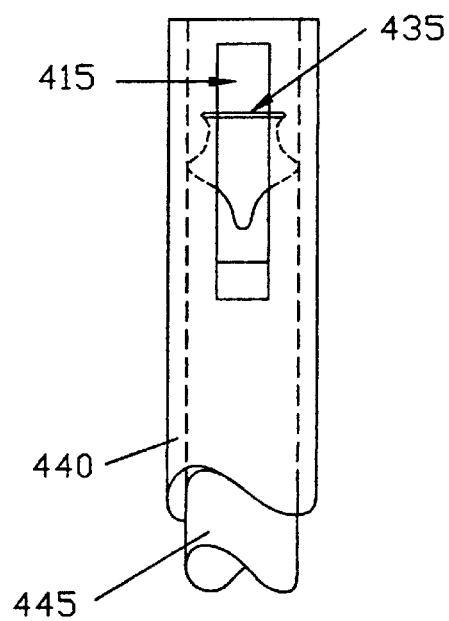
Figure 49:
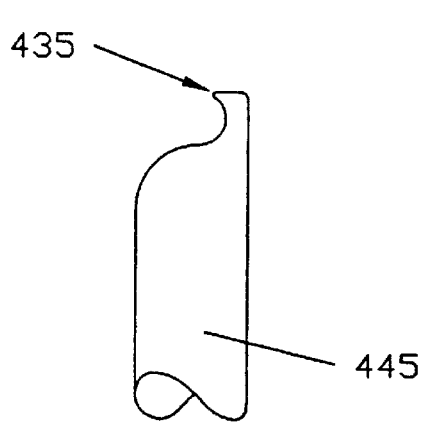
FIGS. 49 and 50 are partial side and front elevational views, respectively, drawn to an enlarged scale, of a core of the embodiment of FIGS. 47 and 48.
Figure 50:
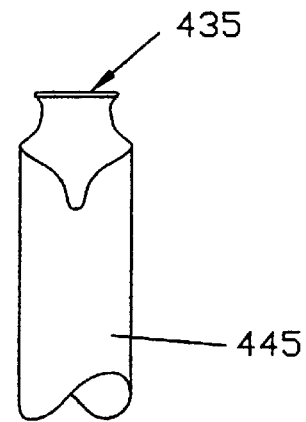

Looking next at FIGS. 36–40, there is shown a knot tier 300 also formed accordance with the present invention. Knot tier 300 comprises a distal end 305 and a proximal end 310. First guide means 315 and second guide means 320 are formed at the distal end of knot tier 300. In a preferred form of the invention, first guide means 315 comprise a bore 325, and second guide means 320 comprise a slot 330. Snagging means 335 are formed at the distal end of knot tier 300, intermediate first guide means 315 and second guide means 320. With the knot tier 300 of FIGS. 36–40, the distal end 305 preferably comprises an outer sleeve 340 and an inner core 345. Sleeve 340 is preferably made of metal and core 345 is preferably made of plastic. The plastic core terminates short of the distal end of the tubular sleeve to form a recess to accommodate the knot (see FIG. 41). Snagging means 335 may comprise the sharp edge at the distal end of core 345.

FIGS. 41–46 illustrate operation of knot tier 300 in advancing, tightening and locking a sliding knot S.

Looking next at FIGS. 47–50, there is shown a knot tier 400 also formed accordance with the present invention. Knot tier 400 comprises a distal end 405 and a proximal end 410. First guide means 415 and second guide means 420 are formed at the distal end of knot tier 400. In a preferred form of the invention, first guide means 415 comprise a bore 425, and second guide means 420 comprise a slot 430. Snagging means 435 are formed at the distal end of knot tier 400, intermediate first guide means 415 and second guide means 420. With the knot tier 400 of FIGS. 47–50, the distal end 405 preferably comprises an outer sleeve 440 and an inner core 445. Sleeve 440 is preferably made of metal and core 445 is preferably made of plastic. The plastic core terminates short of the distal end of the tubular sleeve to form a recess to accommodate the knot (see FIG. 51). Snagging means 435 may comprise the sharp edge at the distal end of core 445.

Figure 51:
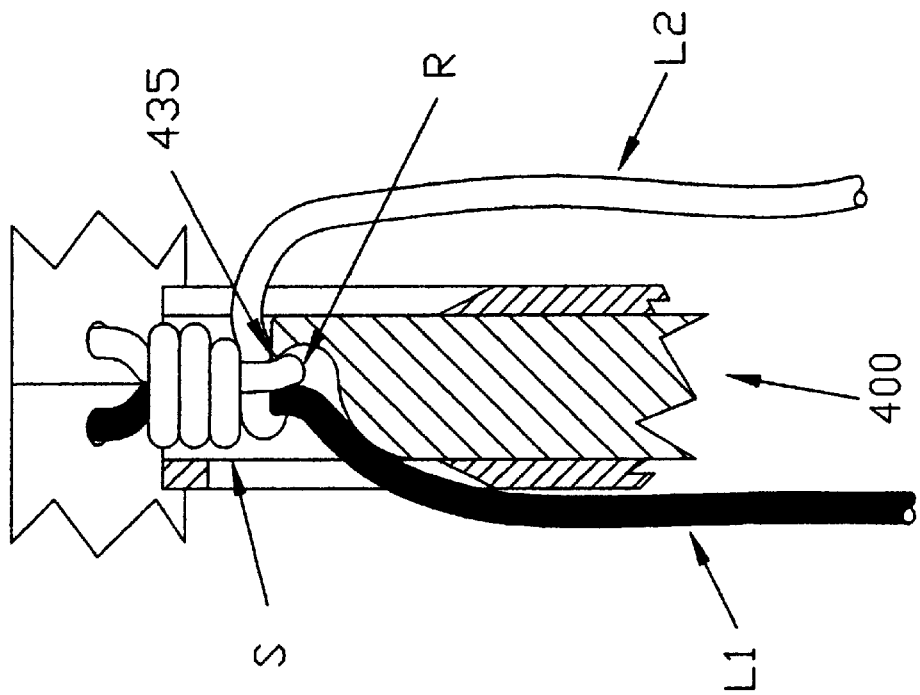
FIG. 51 is a partial, lateral cross-sectional detail view of the embodiment of FIGS. 47–50 engaged with a sliding knot.

FIG. 51 illustrates how knot tier 400 engages a sliding knot S.

In the preferred form of the invention, sliding knot S comprises a proximal locking sliding knot. However, the knot tier will also work for the non-locking sliding knot and the distal locking sliding knot.

In the case of the non-locking sliding knot, the knot is prevented from backing off by positioning the wrapping limb in the slot and pulling on the wrapping limb. Pulling on the wrapping limb will pull the knot against the distal surface of the knot tier and thus tighten the wrappings around the post. The tighter grip of the knot will make it less likely for the knot to back off.

In the case of the distal locking knot, pulling on the wrapping limb will cause the knot to jam against the distal end of the knot tier and the distal portion of the wrapping will cause the post to distort, causing it to lock.

The invention is not limited to the embodiments disclosed above, but encompasses all improvements and substitutions consistent with the principles of the invention.

ADVANTAGES OF THE INVENTION

Numerous advantages are achieved through the provision and use of the present invention.

For one thing, a knot tier is provided which is easy to use, and its associated method of use may be easily taught to surgeons.

For another thing, a knot tier is provided which is capable of generating the desired tension in the loop portion of the knot.

And a knot tier is provided which is capable of locking a sliding knot while the knot is held under the desired tension.

Also, a method of knot tying is provided such that reversing half-hitches on alternating posts are applied without having to re-thread the knot tier.

What is claimed is:

1. A knot tier comprising:
   snagging means for locking a sliding knot in a surgical suture;
   first guide means for guiding a first suture limb associated with the sliding knot; and
   second guide means for guiding a second suture limb associated with the sliding knot;

wherein said first guide means and second guide means converge;

said guide means being selected from a slot, a hole, a sleeve having a slot and a sleeve having a hole.

2. A knot tier according to claim 1 wherein said snagging means is interposed between said first guide means and said second guide means.

3. A knot tier according to claim 2 wherein said snagging means are formed out of plastic.

4. A knot tier according to claim 10 wherein said first guide means is adapted for guiding a first suture limb associated with a sliding knot.

5. A knot tier according to claim 4, said first guide means being selected from a hole, a slot, a sleeve having a hole and a sleeve having a slot.

6. A knot tier according to claim 4 wherein said second guide means is adapted for guiding a second suture limb associated with the sliding knot.

7. A knot tier according to claim 6, wherein said first guide means and said second guide means are generally aligned.

8. A knot tier according to claim 6, wherein said first guide means and said second guide means converge.

9. A knot tier comprising:
a shaft having a distal end and a proximal end;
a handle mounted at the proximal end of said shaft, in the form of a ring, sized to fit the thumb of a user;
first guide means located at the distal end of said shaft, said first guide means being an aperture; and
second guide means located at the distal end of said shaft, said second guide means having two legs in close proximity to said first guide means, said legs angled distally; and
snagging means, wherein said snagging means comprise the crotch of said two legs and the entrance to said second guide means defined by said two legs.

10. A knot tier comprising:
a shaft having a distal end and a proximal end;
a handle mounted at the proximal end of said shaft adapted to fit around a thumb of a user;
a first guide located at the distal end of said shaft, said first guide being an aperture;
a second guide located at the distal end of said shaft, said second guide having two legs in close proximity to said first guide, said legs being angled distally; and
a snagging means comprising a crotch of said two legs and an entrance to said second guide defined by said two legs.

11. A knot tier according to claim 10, wherein said first guide is adapted for guiding a first suture limb associated with a sliding knot.

12. A knot tier according to claim 11, said first guide aperture being selected from a hole, a slot, a sleeve having a hole and a sleeve having a slot.

13. A knot tier according to claim 11 wherein said second guide is adapted for guiding a second suture limb associated with the sliding knot.

14. A knot tier according to claim 13, said second guide being selected from a slot, a hole, a sleeve having a slot and a sleeve having a hole.

15. A knot tier according to claim 14, wherein said first guide and said second guide are generally aligned.

16. A knot tier according to claim 14, wherein said first guide and said second guide converge.

17. A method for tying a slip knot, the method comprising the steps of:

providing a knot tier comprising:
a shaft;
a handle mounted on a proximal end of said shaft;
a first guide located at a distal end of said shaft and comprising an aperture;
a second guide located at the distal end of said shaft, said second guide having two legs in close proximity to said first guide, said legs being angled distally; and
a snagging means comprising a crotch of said two legs and an entrance to said second guide defined by said two legs;
forming a slip knot with a wrapping limb about a post limb and defining a loop, said post limb extending through said aperture, and said wrapping limb extending between said two legs, and said knot being adjacent said snagging means;
cinching the loop to a desired tension by pulling on the post limb and pushing the knot along the post limb; and
locking the knot on the post limb by pulling the wrapping limb, pushing the knot away from the wrapping limb, then relaxing the post limb, to distort the post limb.

18. A method according to claim 17, said locking including snagging a shoulder of the knot.

19. A method according to claim 18, wherein said snagging is achieved with said snagging means.

20. A method according to claim 19, further comprising securing the knot.

21. A method according to claim 20, wherein the securing of the knot comprises forming at least one half-hitch proximate to the knot.

22. A method for tying a slip knot in a surgical suture, and advancing the knot to a remote surgical site removed from an operator, the method comprising the steps of:

providing a knot tier comprising:
a shaft;
a handle mounted on a proximal end of said shaft;
a first guide located at a distal end of said shaft and comprising an aperture;
a second guide located at the distal end of said shaft, said second guide having two legs in close proximity to said first guide, said legs being angled distally; and
a snagging means comprising a crotch of said two legs and an entrance to said second guide defined by said two legs;
forming a slip knot in the suture with a suture wrapping limb about a suture post limb and defining a suture loop, said post limb extending through said aperture, said wrapping limb extending between said two legs, and said knot being adjacent said snagging means;
cinching the suture loop to a desired tension by pulling on the post limb and pushing the knot along the post limb toward the remote site; and
locking the knot on the post limb at the remote site by pulling the wrapping limb, pushing the knot away from the wrapping limb, then relaxing the post limb, to distort the post limb.

23. A method according to claim 22, wherein said locking of said knot includes snagging a shoulder of the knot.

24. A method according to claim 23, wherein said snagging is achieved with said snagging means.

25. A method according to claim 24, further comprising securing the knot.

26. A method according to claim 25, wherein securing the knot comprises forming one or more half-hitches proximate the knot.

27. A method for tying a slip knot in a surgical suture, and advancing the knot to a remote surgical site removed from an operator, the method comprising the steps of:

providing a knot tier comprising:
  a shaft;
  a handle mounted on a proximal end of said shaft and adapted to fit around a thumb of an operator;
  a first guide located at a distal end of said shaft and comprising an aperture;
  a second guide located at the distal end of said shaft, said second guide having two legs in close proximity to said first guide, said legs being angled distally; and
  a snagging means comprising a crotch of said two legs and an entrance to said second guide defined by said two legs;
forming a slip knot in the suture with a suture wrapping limb around a suture post limb and defining a suture loop, said post limb extending through said aperture and proximally along said shaft, the operator permitting said suture post limb to rest on and hang from an operator's finger proximate the operator's thumb, said wrapping limb extending between said two legs, and said knot being adjacent said snagging means;

cinching the suture loop to a desired tension by pulling on the post limb with said finger and pushing the knot with said snagging means along the post limb toward the remote site; and locking the knot on the post limb at the remote site by pulling the wrapping limb, pushing the knot away from the wrapping limb, then relaxing the post limb, to distort the post limb.

28. The method in accordance with claim 27 and including the further step of attaching a weight to said post limb to pull said post limb taught around said operator finger and place tension on said post limb.

29. The method in accordance with claim 28 including the further step of the operator intermittently clinching a hand to move the thumb and finger toward each other to push said shaft distally and pull said post limb proximally, to move said knot ratchet-like toward the remote site.

* * * * *